(12) United States Patent
Richardson et al.

(10) Patent No.: US 11,712,113 B2
(45) Date of Patent: Aug. 1, 2023

(54) INTENSIVE USE FURNITURE

(71) Applicants: Jed C. Richardson, Batavia, IL (US);
Brian Moon, Sycamore, IL (US)

(72) Inventors: Jed C. Richardson, Batavia, IL (US);
Brian Moon, Sycamore, IL (US)

(73) Assignee: Norix Group, Inc., West Chicago, IL (US)

( * ) Notice: Subject to any disclaimer, the term of this patent is extended or adjusted under 35 U.S.C. 154(b) by 599 days.

(21) Appl. No.: 16/792,192

(22) Filed: Feb. 15, 2020

(65) Prior Publication Data

US 2021/0030152 A1    Feb. 4, 2021

Related U.S. Application Data

(63) Continuation-in-part of application No. 15/871,057, filed on Jan. 14, 2018, now Pat. No. 10,980,660, and a continuation-in-part of application No. 16/436,914, filed on Jun. 10, 2019, now abandoned.

(60) Provisional application No. 62/683,013, filed on Jun. 10, 2018.

(51) Int. Cl.
*A47B 96/06* (2006.01)
*A47B 97/00* (2006.01)
*F16B 21/16* (2006.01)

(52) U.S. Cl.
CPC .............. *A47B 96/06* (2013.01); *A47B 97/00* (2013.01); *F16B 21/165* (2013.01); *Y10T 403/592* (2015.01)

(58) Field of Classification Search
CPC ................ A61F 5/3769; A61F 5/3792; Y10T 403/1683; Y10T 403/592; E05B 73/00; F16B 21/165; F16B 12/24; F16B 12/36; F16B 12/54; F16B 12/56; A47B 96/06; A47B 97/00
USPC .................................................... 403/DIG. 4
See application file for complete search history.

(56) References Cited

U.S. PATENT DOCUMENTS

| | | | | |
|---|---|---|---|---|
| 3,037,256 A | * | 6/1962 | Chapman ............... | F16B 21/165 74/18.2 |
| 3,526,382 A | * | 9/1970 | Coker .................... | F16B 21/165 220/756 |
| 3,596,554 A | * | 8/1971 | Low ....................... | F16B 21/165 24/453 |

(Continued)

FOREIGN PATENT DOCUMENTS

| | | | | |
|---|---|---|---|---|
| FR | 2793199 A1 | * | 11/2000 | ......... B60N 2/01533 |
| GB | 549179 A | * | 11/1942 | ............ F16B 21/165 |

*Primary Examiner* — Matthew R Mcmahon
(74) *Attorney, Agent, or Firm* — James D Palmatier; Applied Patent Services, PC

(57) ABSTRACT

An intensive use furniture concealed attachment device for securing furniture in a safe manner having a building bracket attached to the floor or wall and a tab attached to the furniture. The building bracket includes a tab flange and a pin flange. The tab is attached to the furniture in a mounting saddle formed on a mounting surface. The tab is adapted to slidingly engage the building bracket. A hole is formed in the furniture adjacent to the mounting saddle. A guide tube is disposed on the pin flange. A ball pin inserted into the hole and through the guide tube to engage the pin flange and connect the furniture to the building bracket. The tab connected to the building bracket provides support in the x, y and z axis directions.

13 Claims, 24 Drawing Sheets

(56) References Cited

U.S. PATENT DOCUMENTS

| | | | | | |
|---|---|---|---|---|---|
| 3,877,764 | A | * | 4/1975 | Hillier, Jr. | A47B 87/00 312/107 |
| 4,305,614 | A | * | 12/1981 | Holka | B60J 5/101 403/DIG. 4 |
| 4,617,689 | A | * | 10/1986 | Nelson | A47C 17/86 403/252 |
| 5,452,979 | A | * | 9/1995 | Cosenza | B60R 21/2035 411/348 |
| 6,129,324 | A | * | 10/2000 | Blanchard | B60N 2/01533 403/322.2 |
| 6,618,892 | B2 | * | 9/2003 | Schmitt | B08B 9/045 242/593 |
| 6,840,703 | B2 | * | 1/2005 | Blanchard | F16B 19/109 403/322.2 |
| 6,886,377 | B2 | * | 5/2005 | Cohen | A01M 31/02 182/187 |
| 7,914,225 | B2 | * | 3/2011 | Hageman | F16B 19/109 403/322.2 |
| 8,007,059 | B2 | * | 8/2011 | Karl | A47C 19/021 108/147.11 |
| 8,516,732 | B2 | * | 8/2013 | Burnsed, Jr. | F41C 33/002 403/322.2 |
| 9,248,537 | B2 | * | 2/2016 | O'Neill | F16B 13/04 |
| 9,248,714 | B2 | * | 2/2016 | Karasch | B60D 1/488 |
| 10,539,169 | B2 | * | 1/2020 | Ko | A47B 87/02 |
| 2006/0233602 | A1 | * | 10/2006 | Merems | B25G 3/18 403/322.2 |
| 2012/0051835 | A1 | * | 3/2012 | Taylor | F16B 21/165 403/322.2 |

* cited by examiner

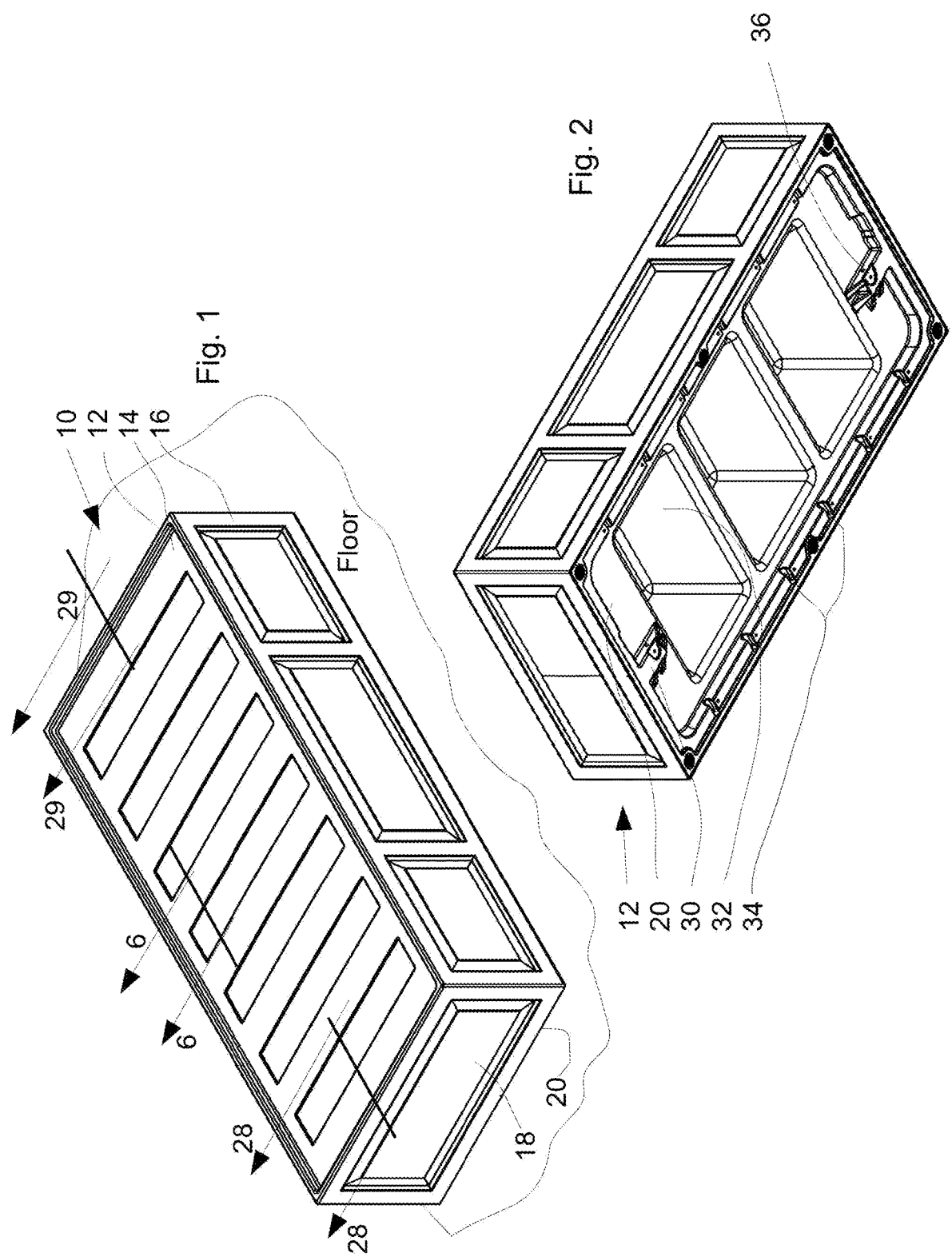

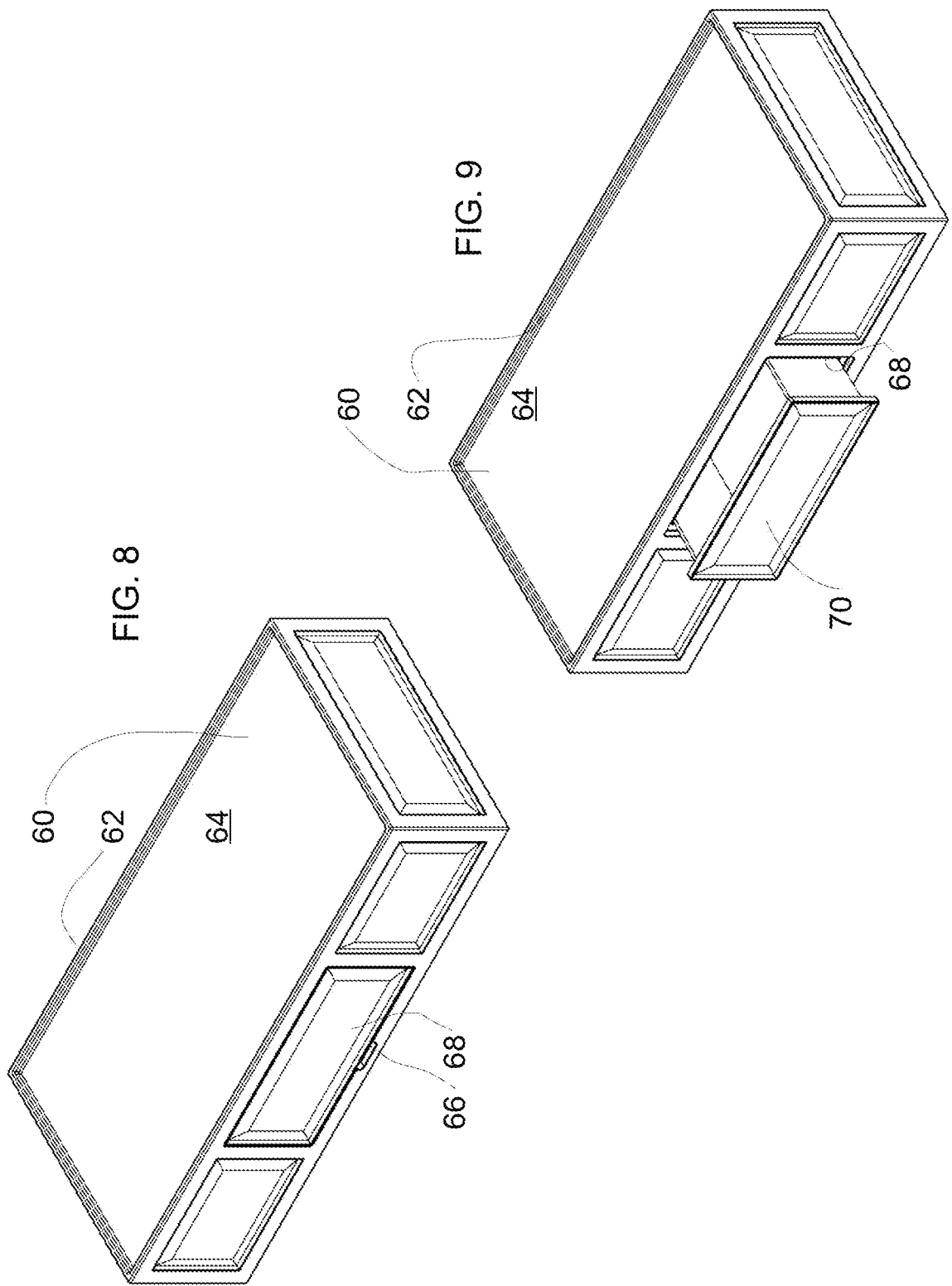

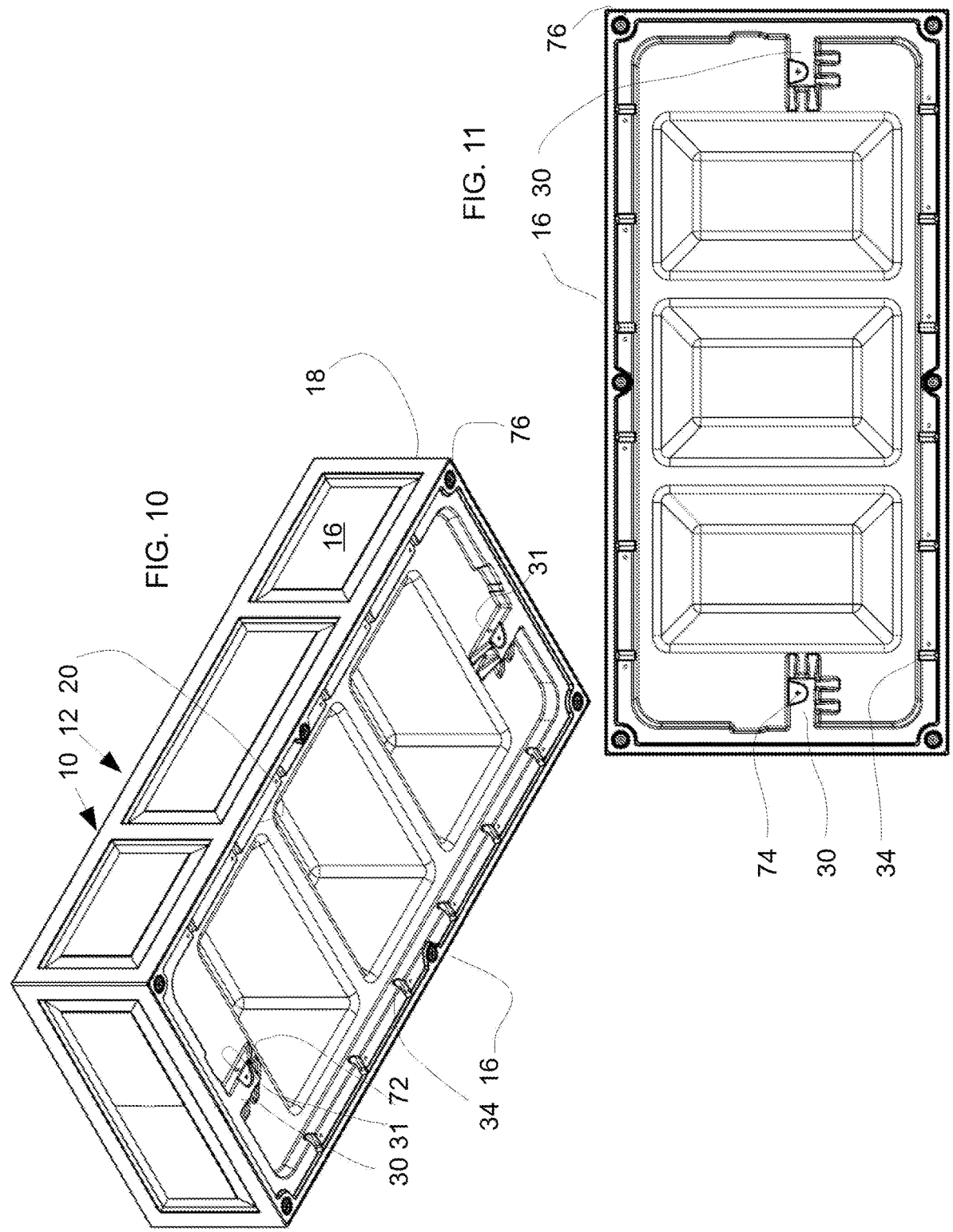

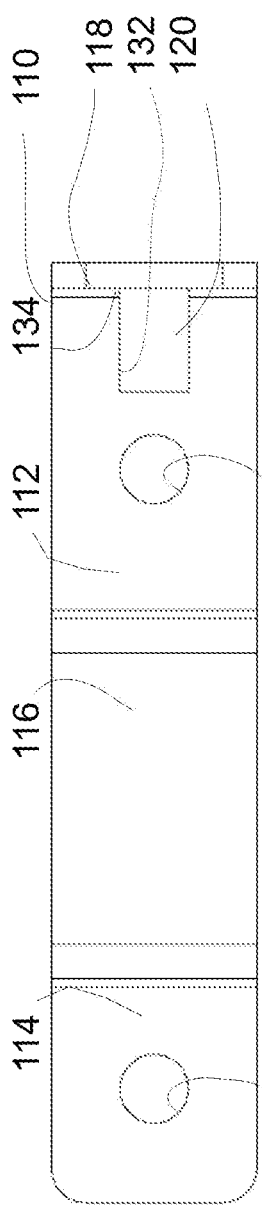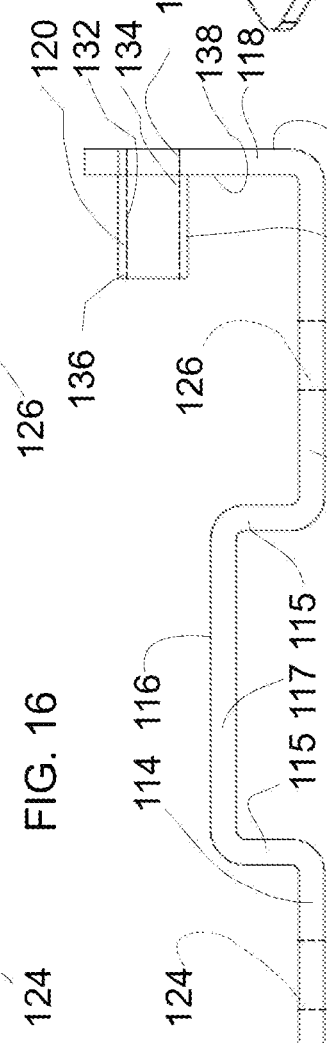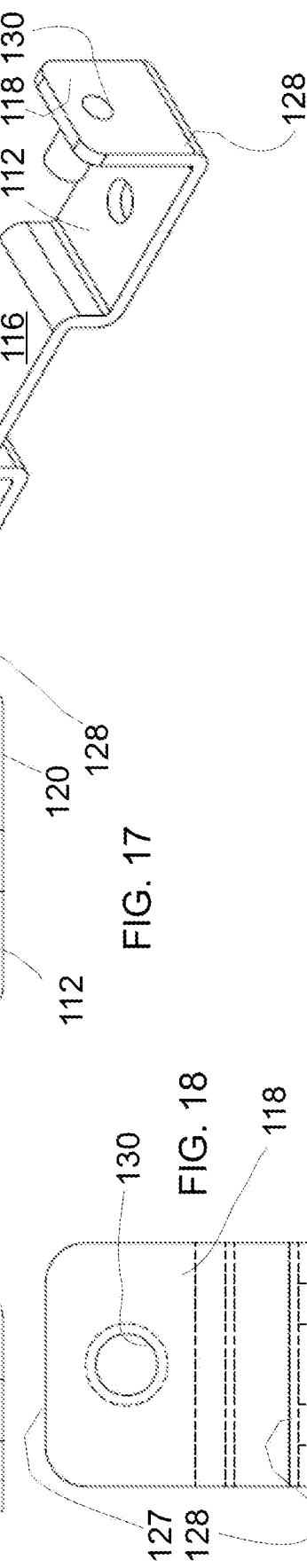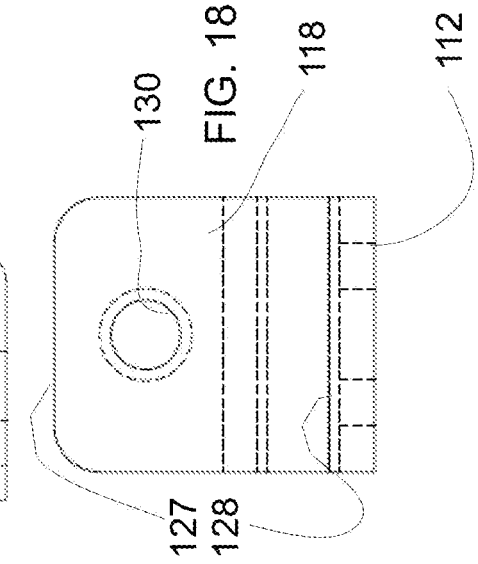

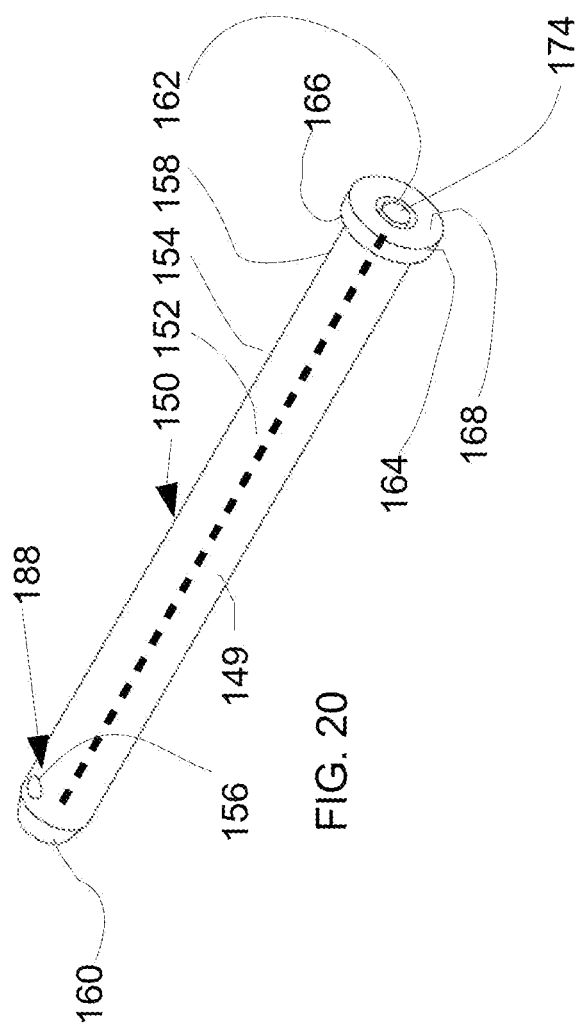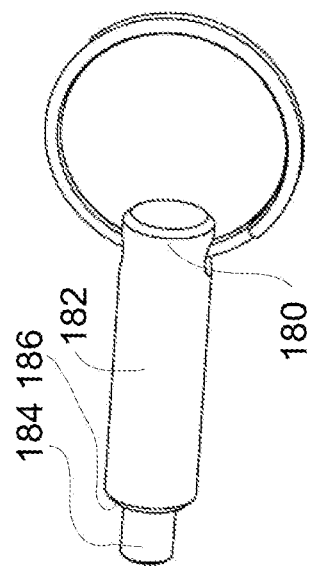

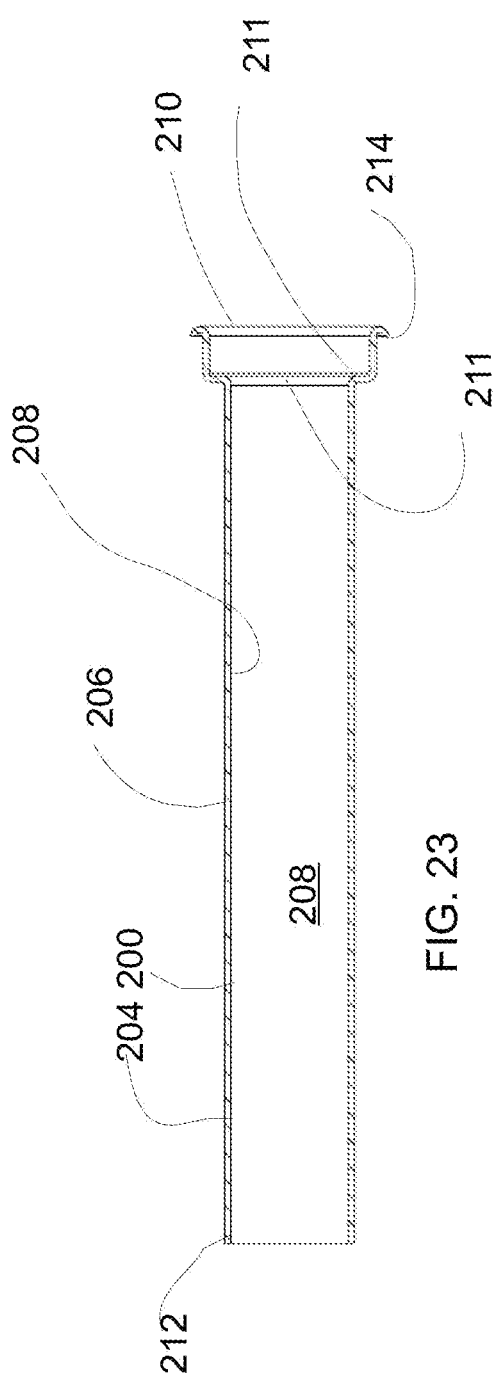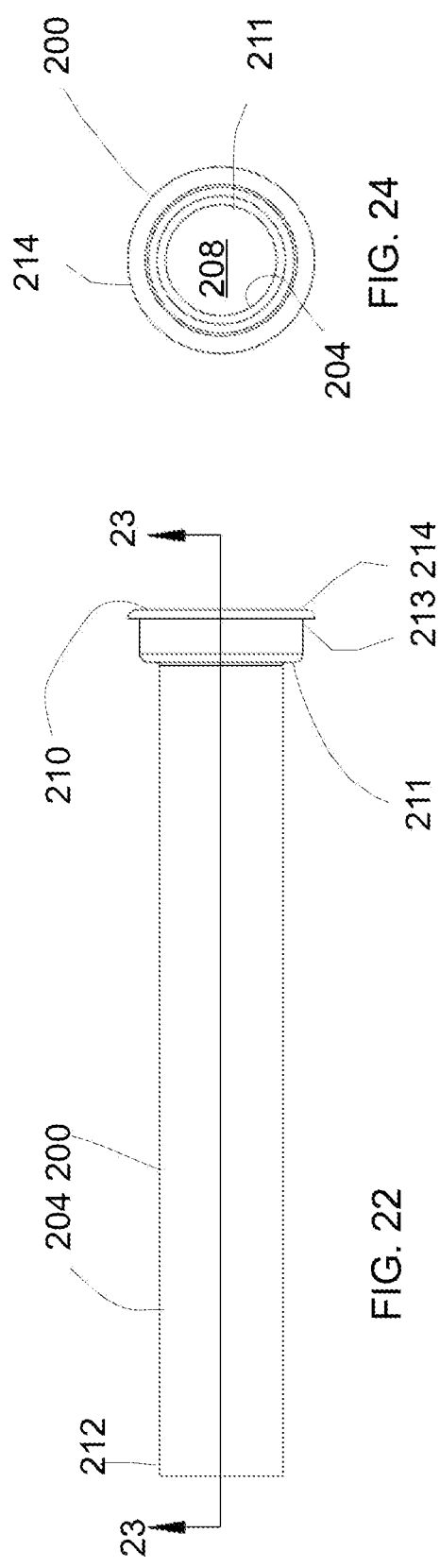

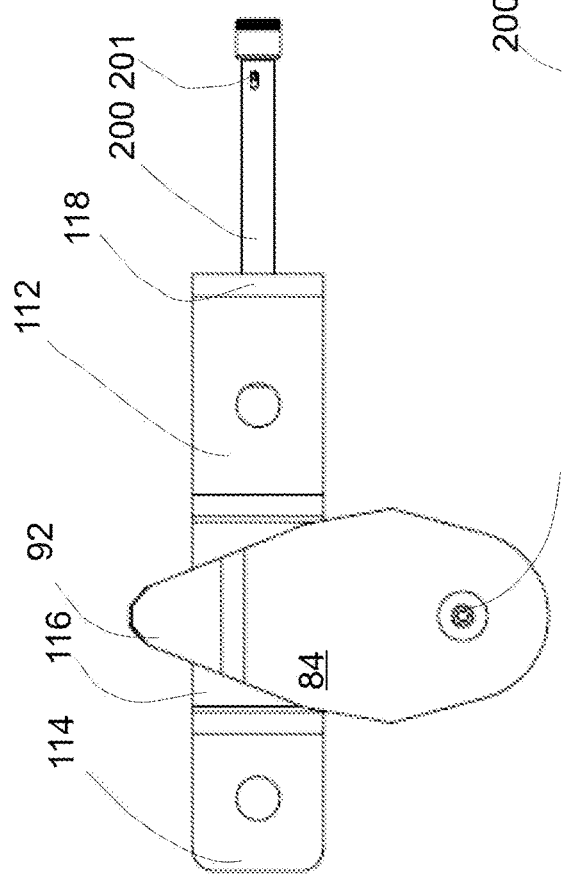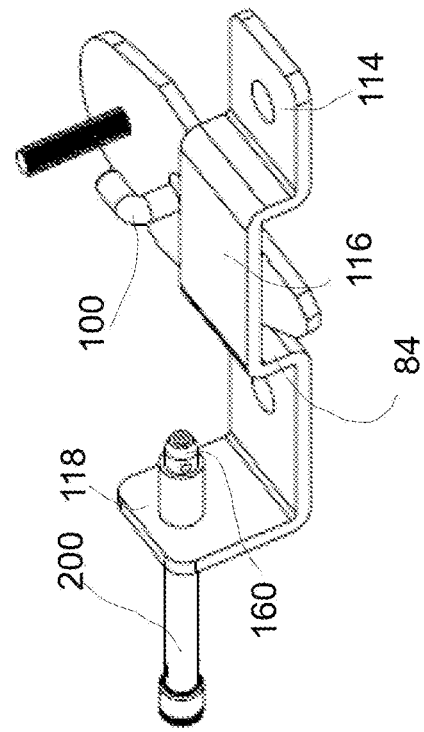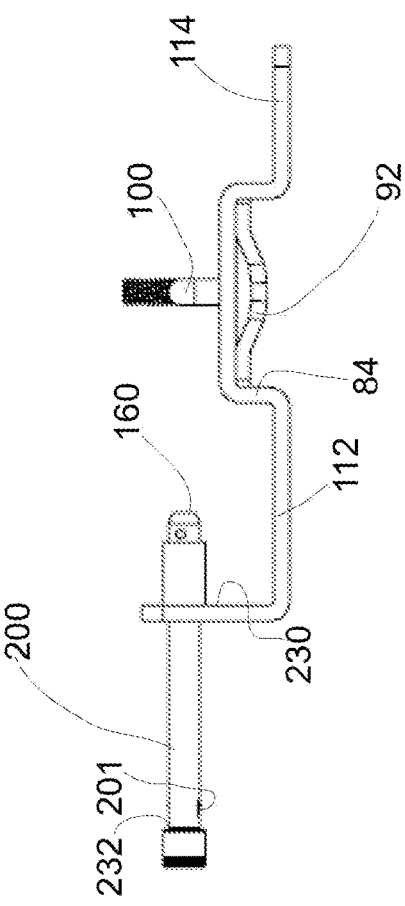

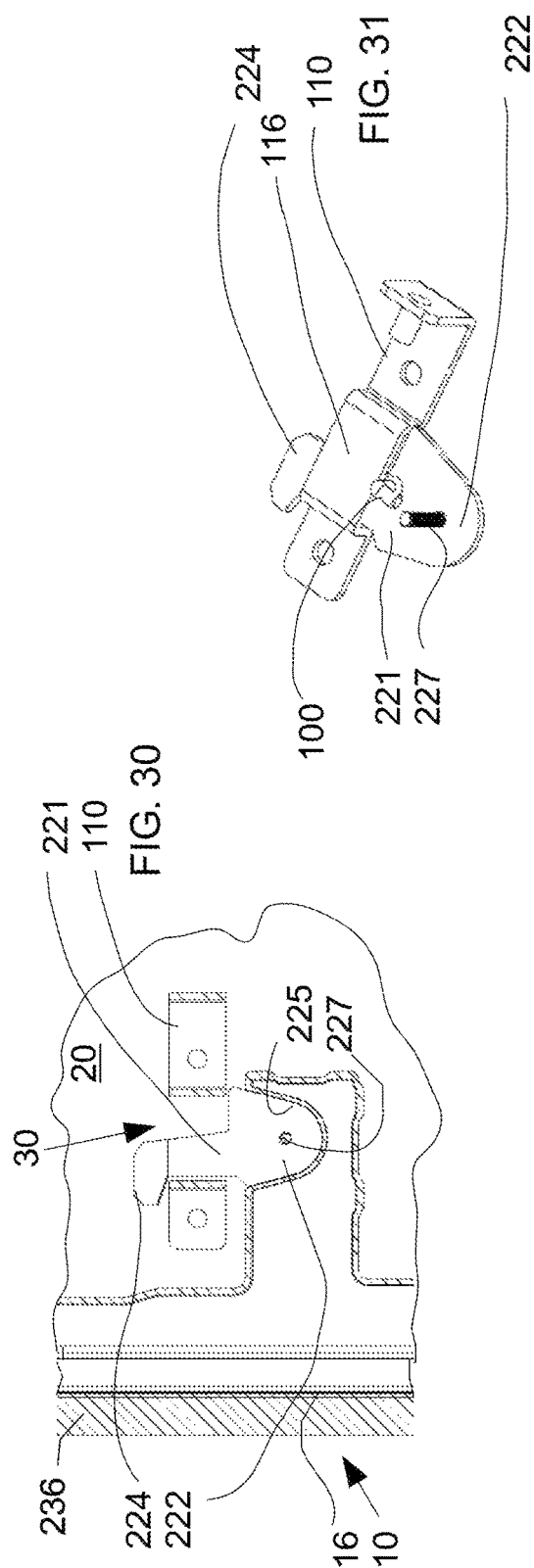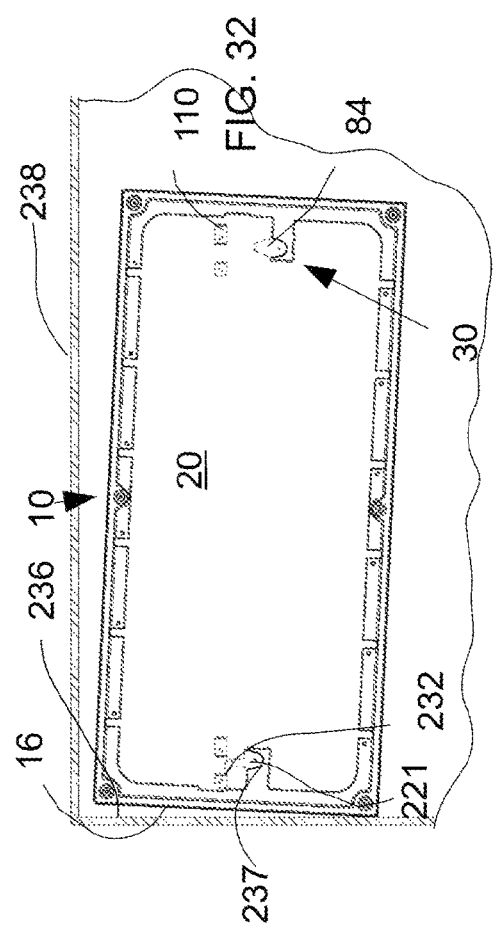

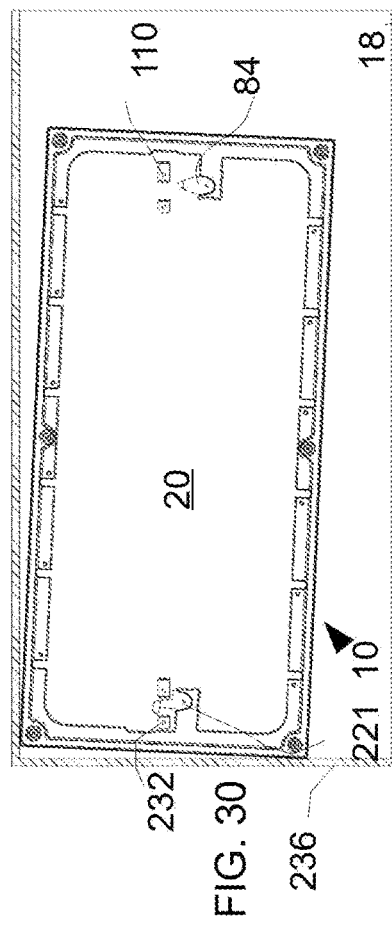
FIG. 30
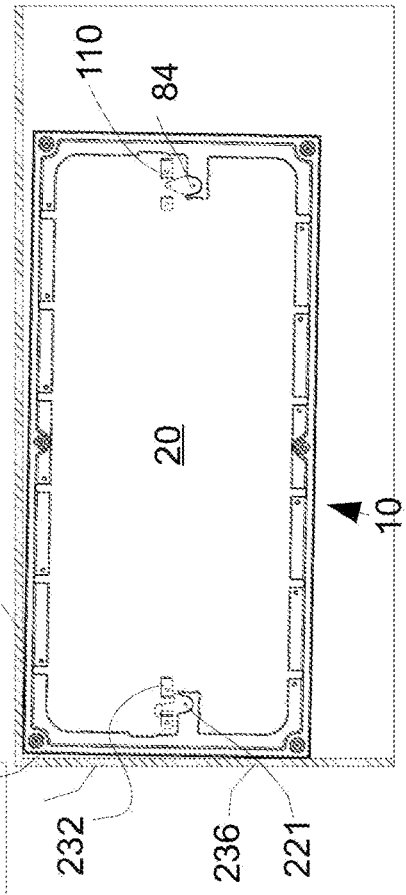
FIG. 33
FIG. 34
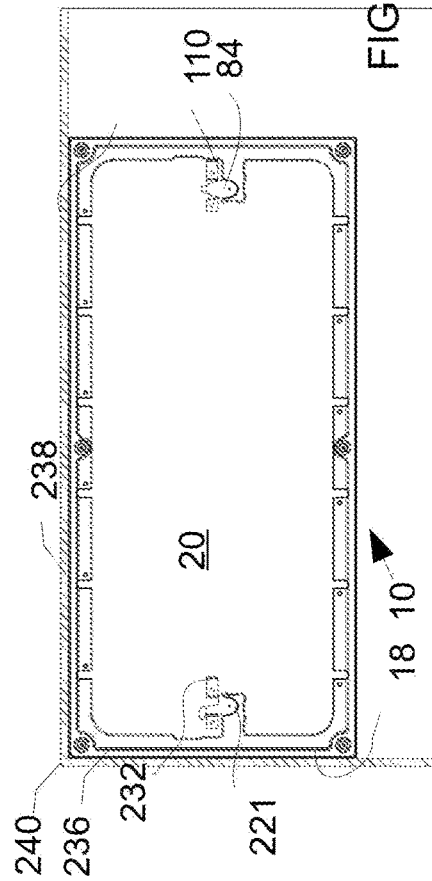
FIG. 35

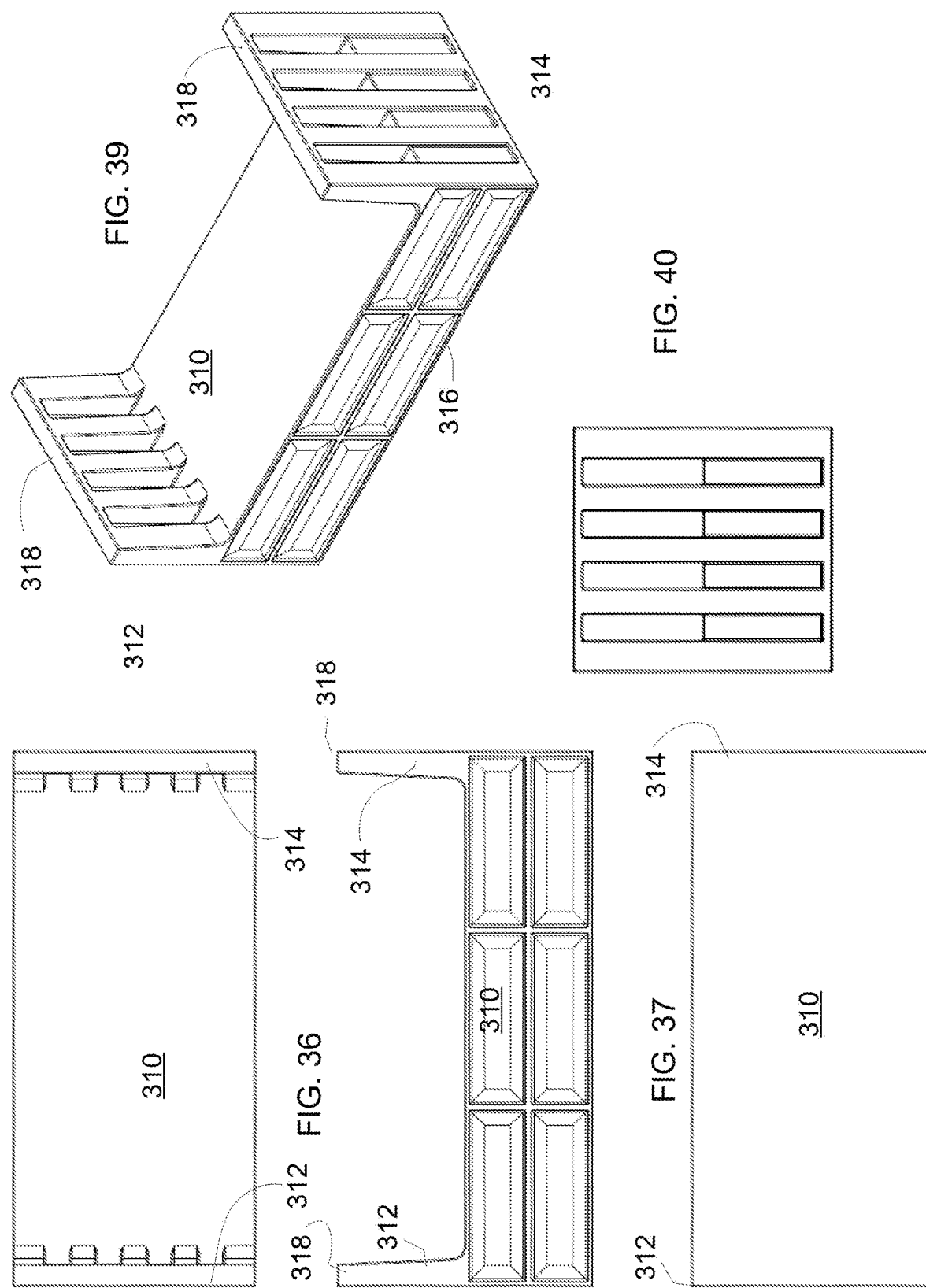

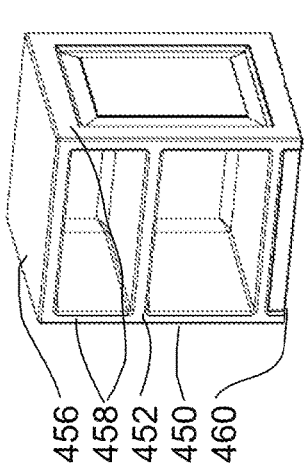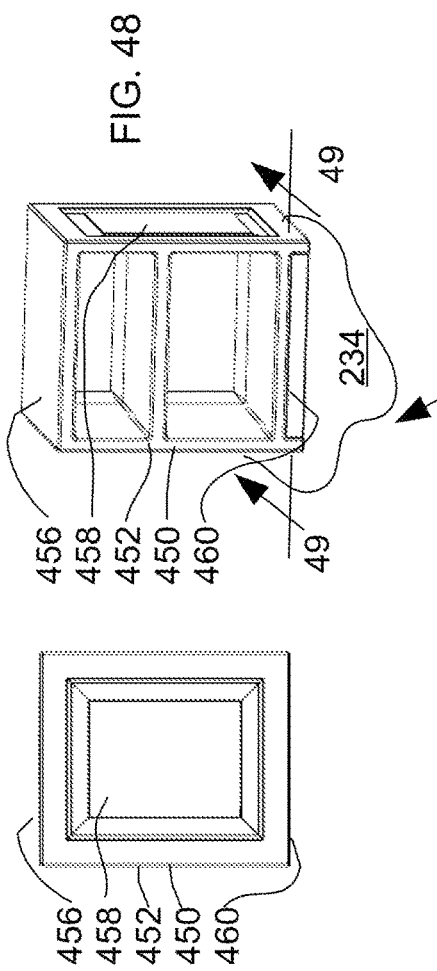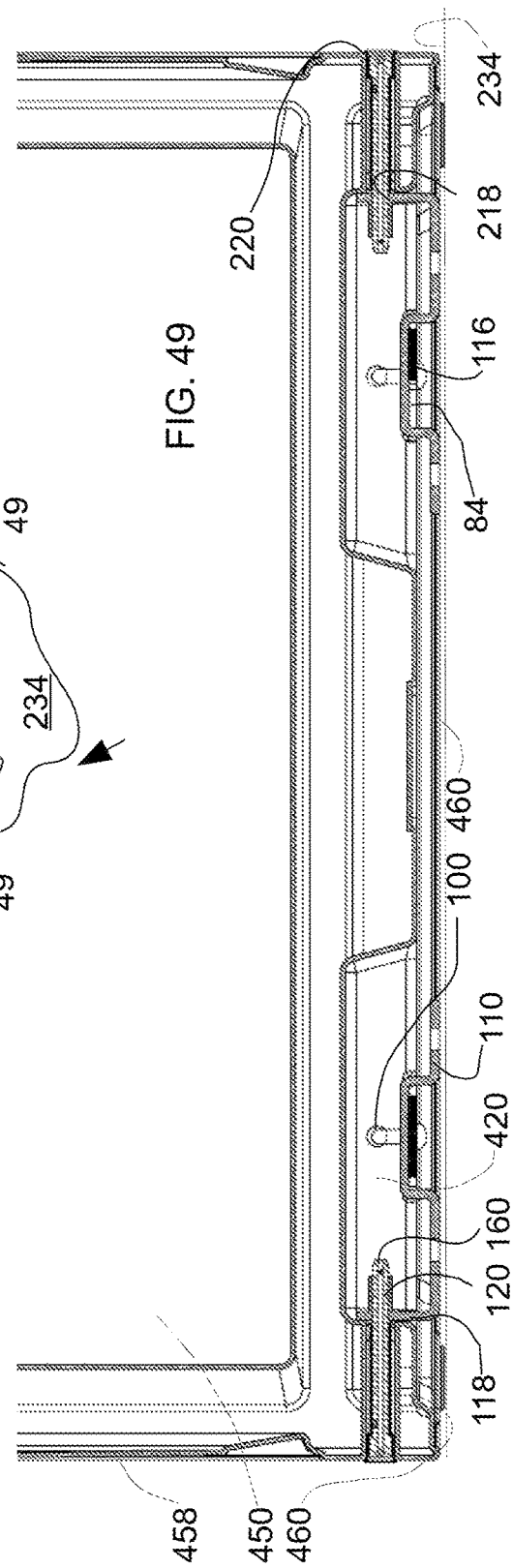

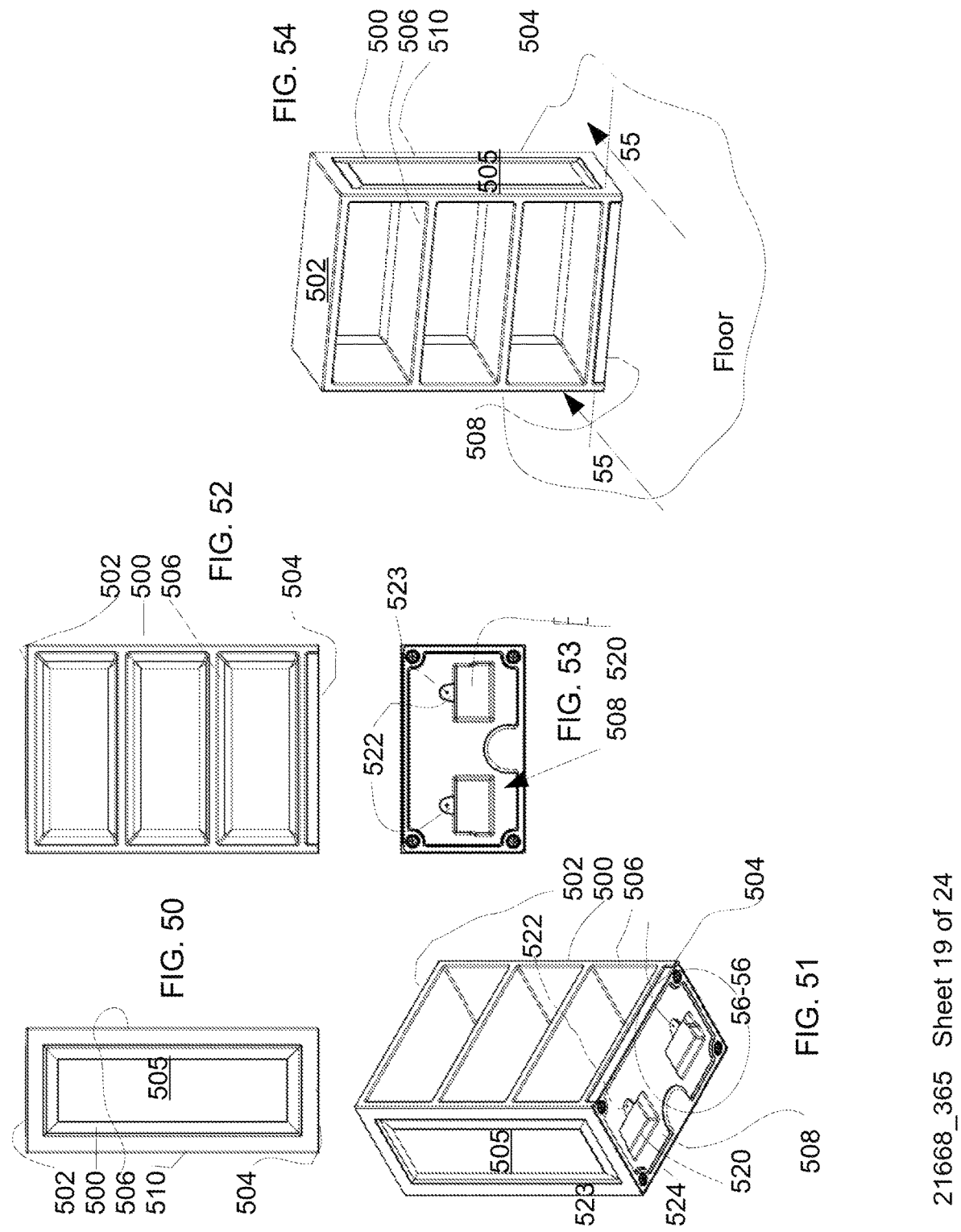

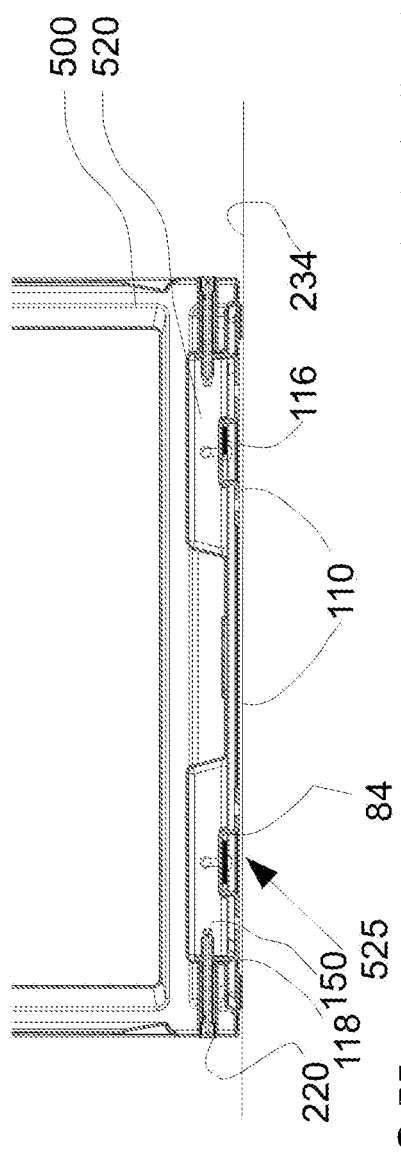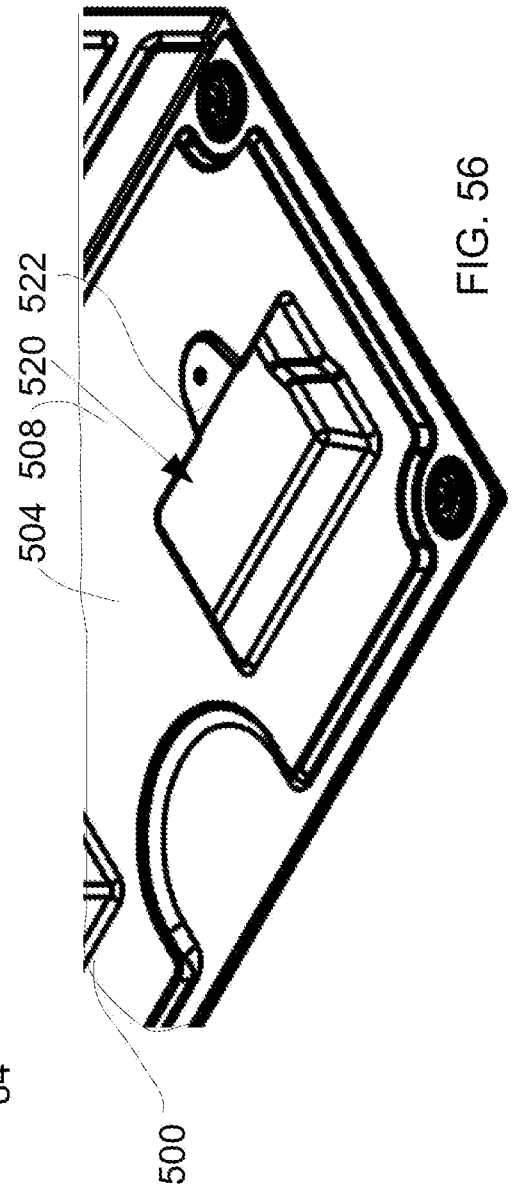

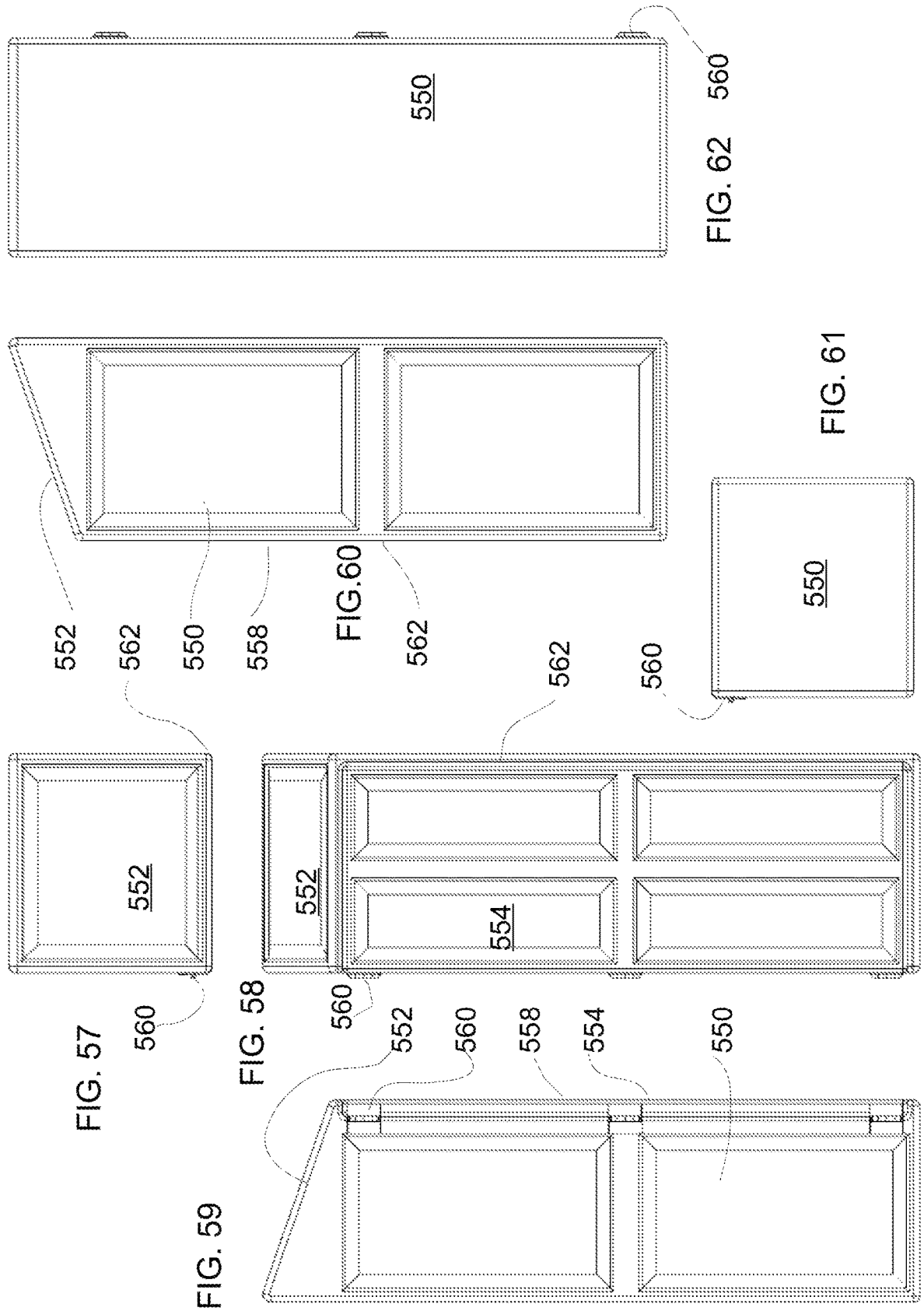

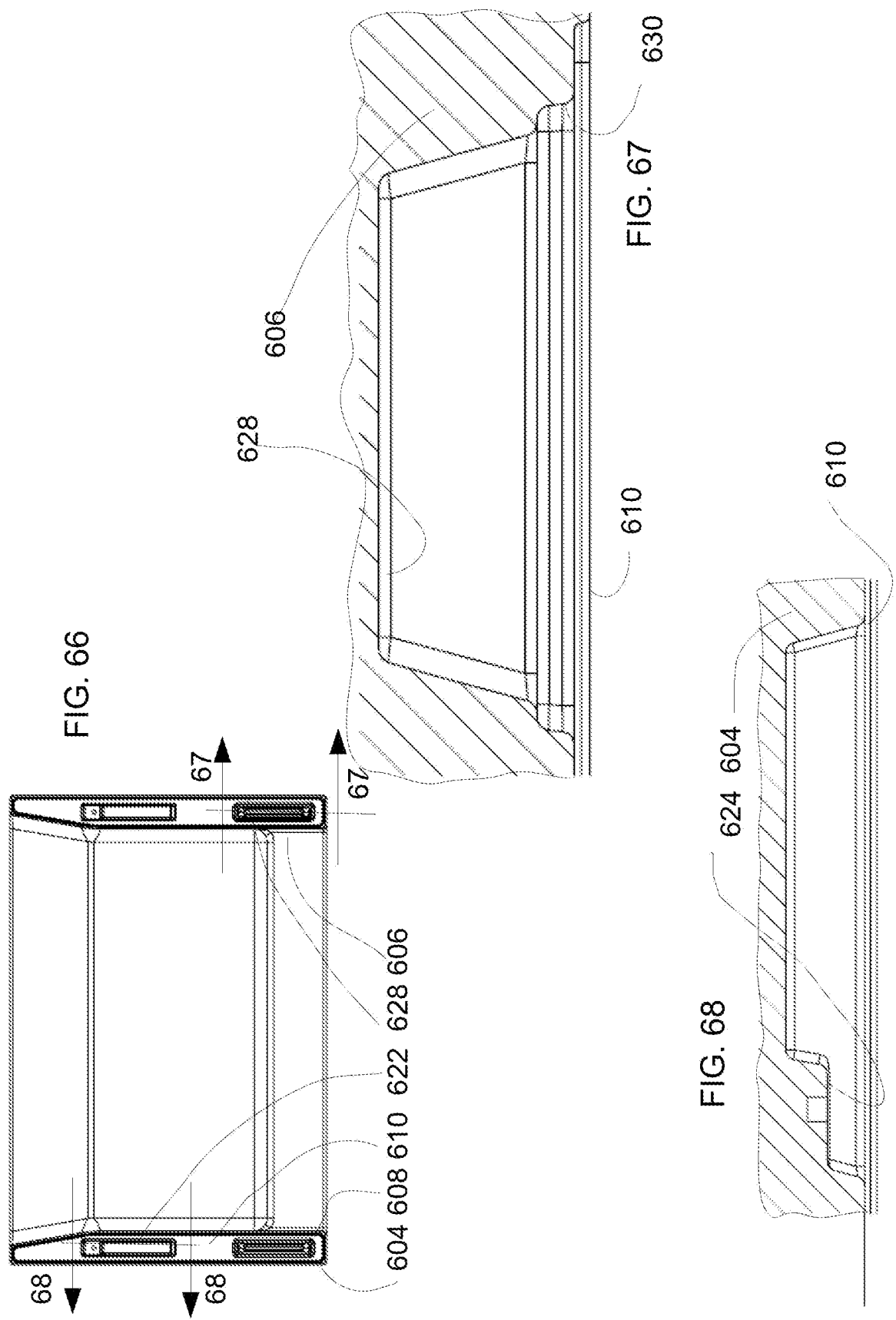

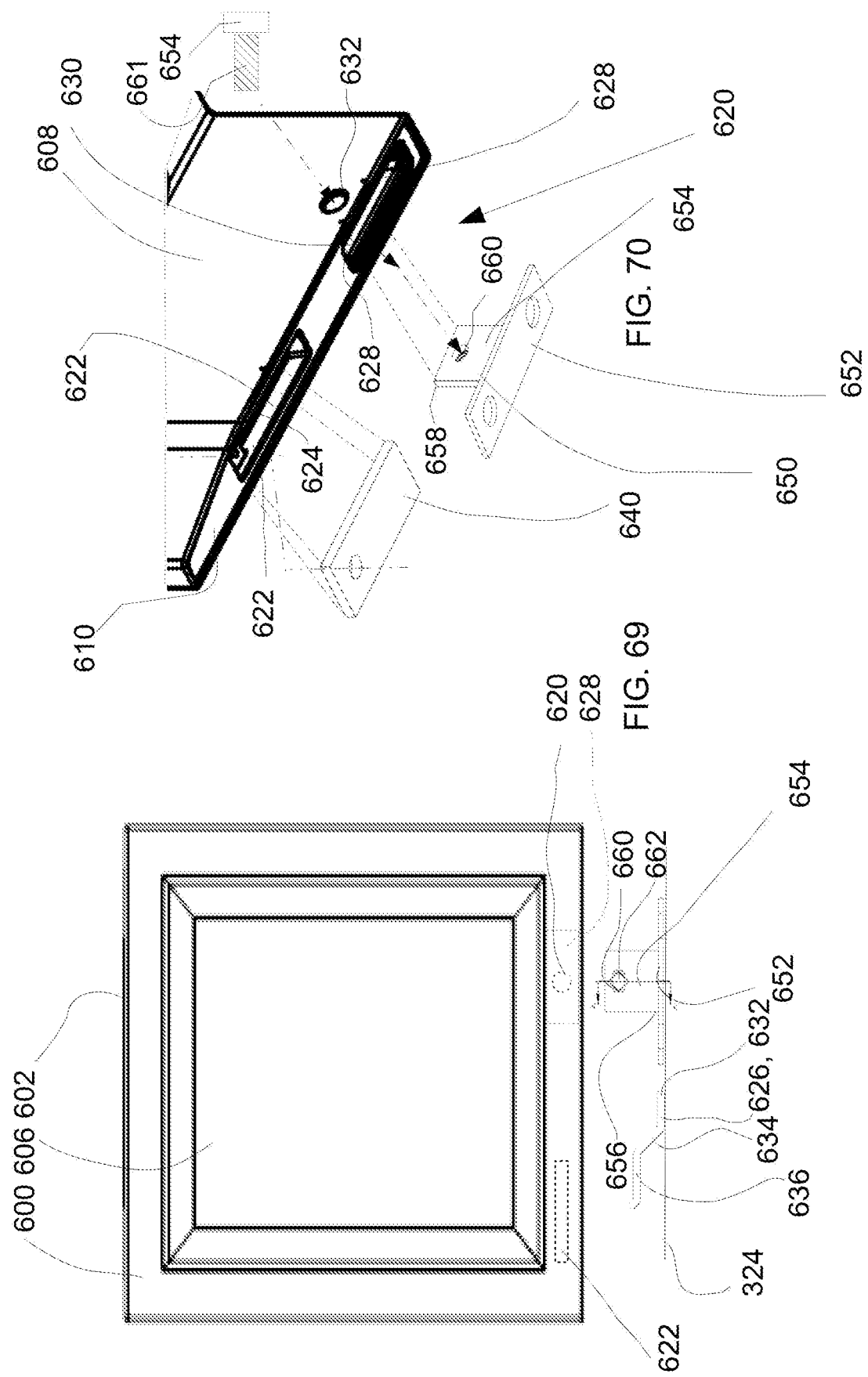

INTENSIVE USE FURNITURE

RELATED APPLICATIONS

This application is a continuation-in-part of co-pending U.S. Non-Provisional application Ser. No. 16/237,522 filed Dec. 31, 2018 for Quick Release Restraint which is a continuation-in-part of co-pending U.S. Non-Provisional application Ser. No. 15/871,057, filed Jan. 14, 2018 for Quick Release Restraint, the contents of which are incorporated by reference in its entirety. This application is also a continuation-in-part of U.S. Non-Provisional U.S. application Ser. No. 16/436,914 (Multi-Color) which is a continuation-in-part of U.S. Provisional Patent Application No. 62/683,013, filed Jun. 10, 2018, and a continuation-in-part of then co-pending U.S. patent application Ser. No. 16/132,425 filed Sep. 16, 2018 which is a continuation of U.S. Provisional Patent Application No. 62/561,202, filed Sep. 20, 2017.

FIELD OF THE INVENTION

The Intensive Use Furniture relates to molded furniture for use in applications of high use in indoor or outdoor environments such as, health care and hospitality facilities.

BACKGROUND OF THE INVENTION

Molded furniture intensive use furniture is designed for use in demanding environments. Facilities housing individuals for recreation or rehabilitation from health or legal problems require comfortable aesthetically pleasing furniture for safely furnishing living quarters, while being durable. Concealed fasteners for assembly and attachment to floor or wall protects the furniture and the user. The furniture must be assembled and attached to a floor or wall without providing removable parts that may be used as a weapon or tool. Securing the furniture to the floor or wall may further reduce safety concerns of both guests and hosts resulting in a safer environment.

Intensive use furniture may be attached to a floor or wall to prevent movement and use of the furniture to cause damage or injury. In the prior art, furniture may have been bolted to the floor or wall or ballasted with weight to make the furniture too heavy to lift. Assembled multipart furniture may have used threaded fasteners as well to attach components such as an arm rest on a chair. Using threaded fasteners to assemble or attach furniture to a floor or wall may offer an opportunity for a user of the furniture to remove the threaded fastener, such as a bolt, and sharpen an end to use as a weapon. Attempts to hide the fasteners may be overcome by persistent users or prevent moving the furniture without damage. Adhering the furniture to the walls or floor may damage the wall or floor and time may degrade the attachment as the adhesives age. Further such gluing down or hiding fasteners may create problems when the facility manager needs to rearrange the furniture.

Intensive use furniture such as disclosed in Karl U.S. Pat. No. 8,007,059 B2, entitled Intensive Use Furniture is created by rotational molding for durability and ease of cleaning. Such creative manufacturing eliminated fasteners for assembling furniture components. But, the traditional bolt down through a flange on the bottom of side walls may leave the head of the bolt exposed on the top of the flange. The one piece, one color furniture unit is not desired for uses such as hospitality and guest services. Therefore, to provide creatively designed furniture, separately manufactured components and additional aesthetic features such as wood-grain and multi-color effects and recessed fastening enabling fixtures, molded into the furniture, make the product more desirable while protecting the user and others.

Wood-grain effect molded into the furniture provides a pleasing aesthetic making the molded furniture seem more comfortable. By creating a contoured pattern on top of a base shell, with a contrasting color, in a molding process may produce simulated, naturally occurring designs such as wood-grain, stone and other external surface finish designs. These aesthetic designs protect the user and facility. The design is part of the molding process and may not separate while in use. No fasteners such as adhesive is used to attach the surface design. The integral molding of the surface design may reduce manufacturing time and labor to produce.

Multi-color molding using techniques such as zone-control within the mold reduce the labor and cost to produce. By producing an integrally molded multi color product, no assembly fasteners or labor may be needed. Molding one area of the furniture component at a time by selectively heating predefined zones of a mold prior to adding plastic resin, reduces manufacturing time and provides a durable product having integrally molded colors together in a one piece furniture component.

Therefore, it is desirable to provide safe furniture for such facilities with aesthetically pleasing characteristics and design for comfortable use. Therefore there is a need to provide an intensive use furniture product without exposed fasteners and designed for concealed, releasable attachment to a mounting surface such as a wall or floor.

BRIEF DESCRIPTION OF THE PRESENT INVENTION

The Intensive Use Furniture is a molded furniture design having a surface attach design which may attach the furniture by a concealed attachment device fixing the furniture to a bracket. For purposes of description, the surface attach design shall be discussed as a floor mount. It should be understood, the surface attach design may be adapted to attach to a wall as well. The recessed link may be a keyed ball pin or a tamper resistant fastener. The floor attach may prevent movement of the furniture in an x, y or z axis direction, that is the x axis may be left to right, y axis may be forward and backward and z axis may be up or lifting the furniture. The floor bracket may include a floor mount portion and a furniture interface portion. A mounting tab on the furniture may be adapted to engage the floor bracket. The x-axis mounting tab engaged with the floor bracket may prevent x-axis or z-axis movement. A y-axis link on the furniture shell may be adapted to engage the floor bracket. The y-axis link attached to the floor bracket may be adapted to prevent y-axis or z-axis movement of the furniture. A tab mount portion molded into the furniture may be adapted to receive the x-axis tab.

The tab mount portion may comprise a shaped landing portion, a finger hole and a furniture bolt hole. The x-axis mounting tab may comprise a generally flat bracket portion, a finger link and a tab bolt hole. The bracket portion having a furniture end, a bracket end, a floor surface and a furniture surface. The furniture end and the bracket end aligned in a generally y axis orientation. The furniture surface on the shaped landing portion. The finger link on the bracket portion comprising a first end on the furniture surface and a second end spaced from the furniture surface. The second end extending into the finger hole. A threaded fastener extending through the tab bolt hole into the furniture bolt hole. The threaded fastener having a head bearing on the floor surface whereby the x-axis mounting tab is retained on the furniture.

The y-axis link may be aligned in a generally x-axis orientation. The y-axis link may be on the furniture and attached to the floor bracket. y-axis link The y-axis link may use a means to attach to fix the furniture to the floor bracket. The means to attach may include a threaded fastener, a ball pin or other device on the furniture and removably attached to the floor bracket. The y-axis link may have a tamper resistant interface. The tamper resistant interface may be a tamper resistant head or a keyed actuator or other means.

The furniture skin may comprise a plurality of layers. The skin is formed in a mold having a surface effect mold portion comprising a first predetermined relief pattern etched in the product surface to simulate a desired surface finish. The mold may further comprise a structural effect mold portion comprising a second predetermined pattern etched in the product surface to simulate an assembly of boards or rocks making up the furniture. The furniture skin may comprise one piece penetration resistant shell comprising a surface effect furniture portion and a structural effect furniture portion. The surface effect furniture portion on top of the structural effect furniture portion whereby the outer skin may appear to be formed of boards, the boards having a wood grain pattern thereon. a thin, outer, soft touch layer of a clear or translucent polymer. A surface effect layer under the soft touch layer may comprise a wood grain effect comprising a thin layer of plastic having a first color. The surface effect layer may comprise a translucent layer. The skin may further comprise a base layer of a plastic such as polyethylene having a second color. The base layer may further comprise inner support ribs extending into the shell. The inner support ribs disposed adjacent to the second predetermined pattern contours to imitate rocks or board shapes. These rock or board shapes The skin may further comprise a foamed layer inside of the polyethylene layer. The foamed layer comprising ribs extending away from the polyethylene layer. The ribs generally aligned with the contours in the polyethylene layer. Integrally molding a surface design saves time and money but the results must look authentic to provide an aesthetic impression. Wood Grain design is particularly pleasing for Lounge or Guest chairs, stacking chairs and floor attached chairs. Multi-Color designs appeal to play or informal areas.

The above description sets forth, rather broadly, the more important features of the present invention so that the detailed description of the preferred embodiment that follows may be better understood and contributions of the present invention to the art may be better appreciated. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE SEVERAL
VIEWS OF THE DRAWING

FIG. 1 is a top perspective view of the intensive use bed.
FIG. 2 is a bottom perspective view of the bed of FIG. 1.
FIG. 3 is a top plan view of the bed of FIG. 1.
FIG. 4 is a front elevation view of the bed of FIG. 1.
FIG. 5 is a side elevation view of the bed of FIG. 1.
FIG. 6 is a section view taken at approximately 6-6 of FIG. 1.
FIG. 7 is an alternate section view taken at approximately 6-6 of FIG. 1.
FIG. 8 is a top perspective view of an alternate embodiment intensive use bed.
FIG. 9 is a top perspective view of the alternate embodiment intensive use bed of FIG. 8 showing the storage drawer.
FIG. 10 is a bottom perspective view of the bed of FIG. 8.
FIG. 11 is a bottom plan view of the bed of FIG. 8.
FIG. 12 is a close up view of the mounting saddle with the bracket attached.
FIG. 13 is a top plan view of a mounting tab.
FIG. 14 is a side elevation view of the mounting tab of FIG. 13.
FIG. 15 is a top perspective view of the mounting tab of FIG. 13.
FIG. 16 is a top plan view of a mounting bracket.
FIG. 17 is a side elevation view of the mounting bracket of FIG. 1.6
FIG. 18 is an end elevation view of the mounting bracket of FIG. 16.
FIG. 19 is a top perspective view of the mounting bracket of FIG. 16.
FIG. 20 is a perspective view of a ball pin.
FIG. 21 is an exploded view of the pin of FIG. 20 with retracting tool.
FIG. 22 is a front elevation of a pin tube.
FIG. 23 is a section view taken at approximately 23-23 of FIG. 22.
FIG. 24 is a mounting end view of the tube of FIG. 22.
FIG. 25 is a top plan view of the mounting tab of FIG. 13 engaged to the mounting bracket of FIG. 18.
FIG. 26 is a top perspective view of the mounting tab of FIG. 13 engaged to the mounting bracket of FIG. 18.
FIG. 27 is a side elevation view view of the mounting tab of FIG. 13 engaged to the mounting bracket of FIG. 18.
FIG. 28 is a section view taken at approximately 28-28 of FIG. 1.
FIG. 29 is a section view taken at approximately 29-29 of FIG. 1.
FIG. 30 is a top plan view of a dog leg tab.
FIG. 31 is a perspective view of the dog leg tab of FIG. 30.
FIG. 32 is a first step mounting an end wall of the bed of FIG. 1 against a wall.
FIG. 33 is a second step mounting an end wall of the bed of FIG. 1 against a wall.
FIG. 34 is a third step mounting an end wall of the bed of FIG. 1 against a wall.
FIG. 35 is a fourth step mounting an end wall of the bed of FIG. 1 against a wall.
FIG. 36 is a top plan view of a second alternate intensive use bed.
FIG. 37 is a side elevation view of the bed of FIG. 30.
FIG. 38 is a bottom plan view of the bed of FIG. 30.
FIG. 39 is a top perspective view of the bed of FIG. 30.
FIG. 40 is an end elevation view of the bed of FIG. 30.
FIG. 41 is a top perspective view of a third alternate embodiment intensive use bed.
FIG. 42 is a top plan view of the bed of FIG. 40.
FIG. 43 is a side elevation view of the bed of FIG. 40.

FIG. 46 is a side elevation view of an intensive use nightstand.

FIG. 47 is a top perspective view of the intensive use nightstand of FIG. 46.

FIG. 48 is a front perspective view of the intensive use nightstand of FIG. 46.

FIG. 49 is a section view taken at approximately 49-49 of FIG. 46.

FIG. 50 is a side elevation view of an intensive use bookshelf.

FIG. 51 is a bottom perspective view of the intensive use bookshelf of FIG. 50

FIG. 52 is a front elevation view of the intensive use bookshelf of FIG. 50.

FIG. 53 is a bottom plan view of the intensive use bookshelf of FIG. 50.

FIG. 54 is a top perspective view of the intensive use bookshelf of FIG. 50.

FIG. 55 is a section view taken at approximately 55-55 of FIG. 54.

FIG. 56 is a bottom perspective view of the intensive use bookshelf of FIG. 50.

FIG. 57 is a top plan view of an intensive use wardrobe.

FIG. 58 is a front elevation view of the wardrobe of FIG. 57.

FIG. 59 is a hinge side elevation view of the wardrobe of FIG. 57.

FIG. 60 is a handle side elevation view of the wardrobe of FIG. 57.

FIG. 61 is a bottom plan view of the wardrobe of FIG. 57.

FIG. 62 is a back elevation view of the wardrobe of FIG. 57.

FIG. 66 is a bottom plan view of the desk of FIG. 63.

FIG. 67 is a section view taken at approximately 67-67 of FIG. 66.

FIG. 68 is a section view taken at approximately 68-68 of FIG. 66.

FIG. 69 is a front exploded side elevation view of the desk of FIG. 63.

FIG. 70 is a bottom perspective exploded view of the desk of FIG. 63.

DETAILED DESCRIPTION OF THE INVENTION

Figure 3:
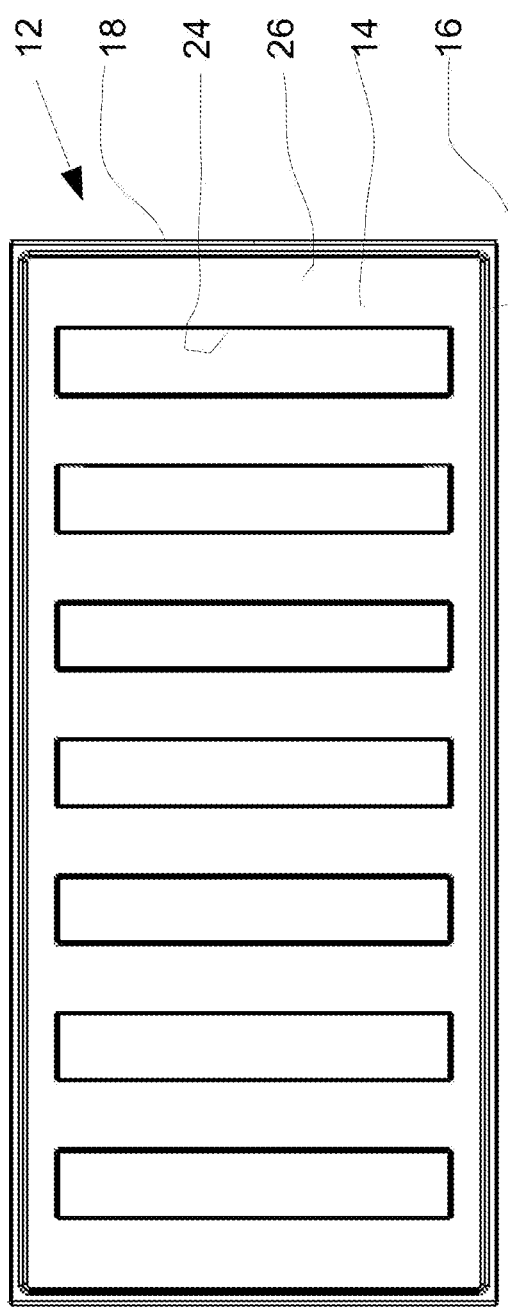

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention. It is to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting. It should be appreciated that the invention can be used for any suitable.

Referring to FIG. 1, an intensive use furniture piece 10 such as bed 12 may have a top 14 sidewalls 16, end walls 18 and a bottom 20 mounted on a floor. The top 14 may comprise a mattress pocket 22 and a ridge 24 formed in the top surface.

Referring to FIG. 2, the bed 12 may further comprise a bottom 20 having a mounting saddle 30 and a plurality of support openings 32. Support openings 32 extend inward to the hollow interior to a location adjacent the mattress pocket 22. Notches 34 are formed in the outer perimeter of the bottom 20.

Figure 4:
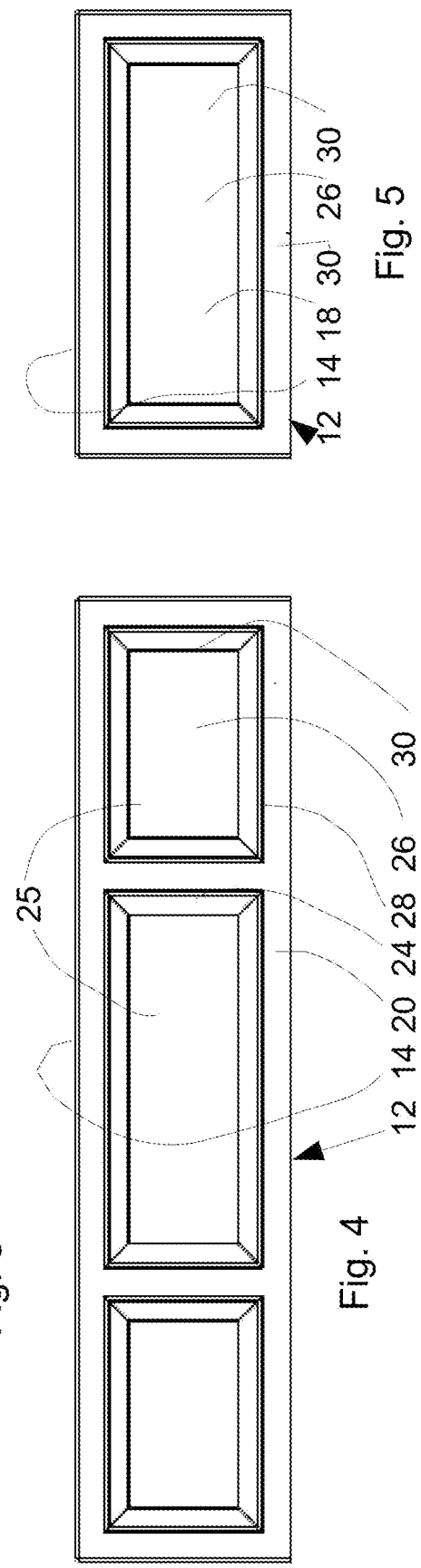
Figure 5:
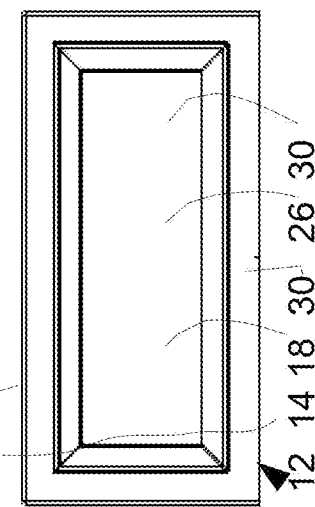

Referring to FIGS. 3-5, the bed 12 may comprise support contours 24 formed in a repeating pattern on the top 14 and a raised panel portion 25 on side walls 16 and end walls 18. The wood-grain layer 26 longitudinal lines horizontally 28 between and the walls 18 or alternatively, may extend vertically 30 between the top 14 in the bottom 20.

Figure 6:
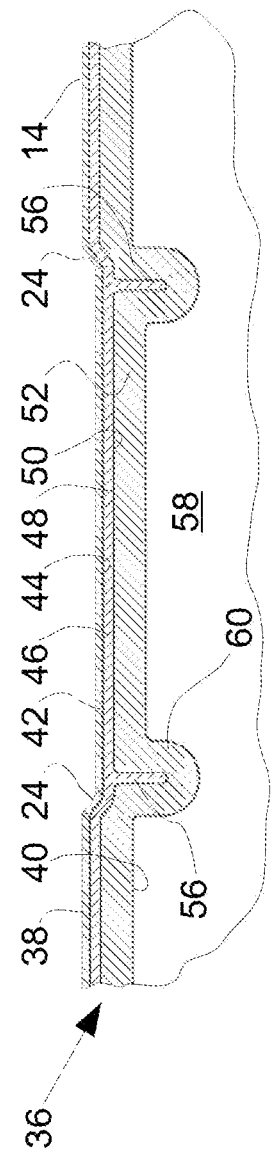
Figure 7:
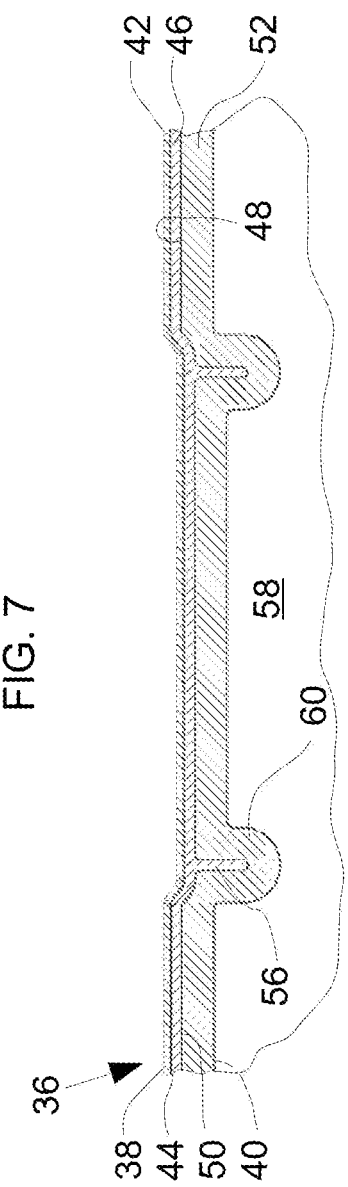

Referring to FIGS. 6-7, a cutaway taken at approximately 6-6 of FIG. 1 shows the cross section of the outer shell 36 having a shell outside 38 and a shell inside 40. A first translucent layer 42 comprising a polyethylene compound such as is available at Mold In Graphics of Clarkdale, Ariz., such as Color In Systems having a first color is disposed on the shell outside 38. The first translucent layer 42 may comprise an inner surface 44 bonded to a second base layer 46 comprising a polyethylene or similar material. The second base layer 46 may comprise an outside surface 48 bonded to the first translucent layer 42. The second base layer 46 may further comprise an inside surface 50 bonded to a third foamed layer 52 comprising a foamed plastic material such as polyethylene.

Continuing to refer to FIGS. 6-7, the foamed polyethylene layer 52 may be molded onto second base layer 46. The foamed polyethylene layer 52 may further comprise shell inside 40 surrounding the hollow interior 58. The contour 24 in the outer surface 38 extends through first translucent layer 42 and the second base layer 46. Adjacent to the contour 24, the second base layer 46 may comprise an attach rib 56 extending into the open interior 58 and increasing the attachment area between second base layer 46 and foamed layer 52. The attach rib 56 is surrounded by the foamed layer 52 forming support rib 60 on the shell inside 40.

Referring to FIGS. 8-9, an alternative embodiment of the intensive use in bed 60 comprising retaining ridge 62 surrounding mattress support surface 64. Handle opening 66 may be used to access storage compartment 68 which may comprise a drawer 70 attached to the bed 60.

Referring to FIGS. 10-11, furniture piece 10 may further comprise a mounting saddle 30 formed in the bottom 20. Mounting saddle 30 further comprises a finger hole 31, tab bolthole 72 and may have a screw hole 74 opening to the bottom 20. The saddle 30 may be disposed adjacent one or both and end walls 18 and spaced generally between sidewalls 16. Restraint mount 34 is formed as a channel generally perpendicular to the respective sidewall 16.

Figure 12:
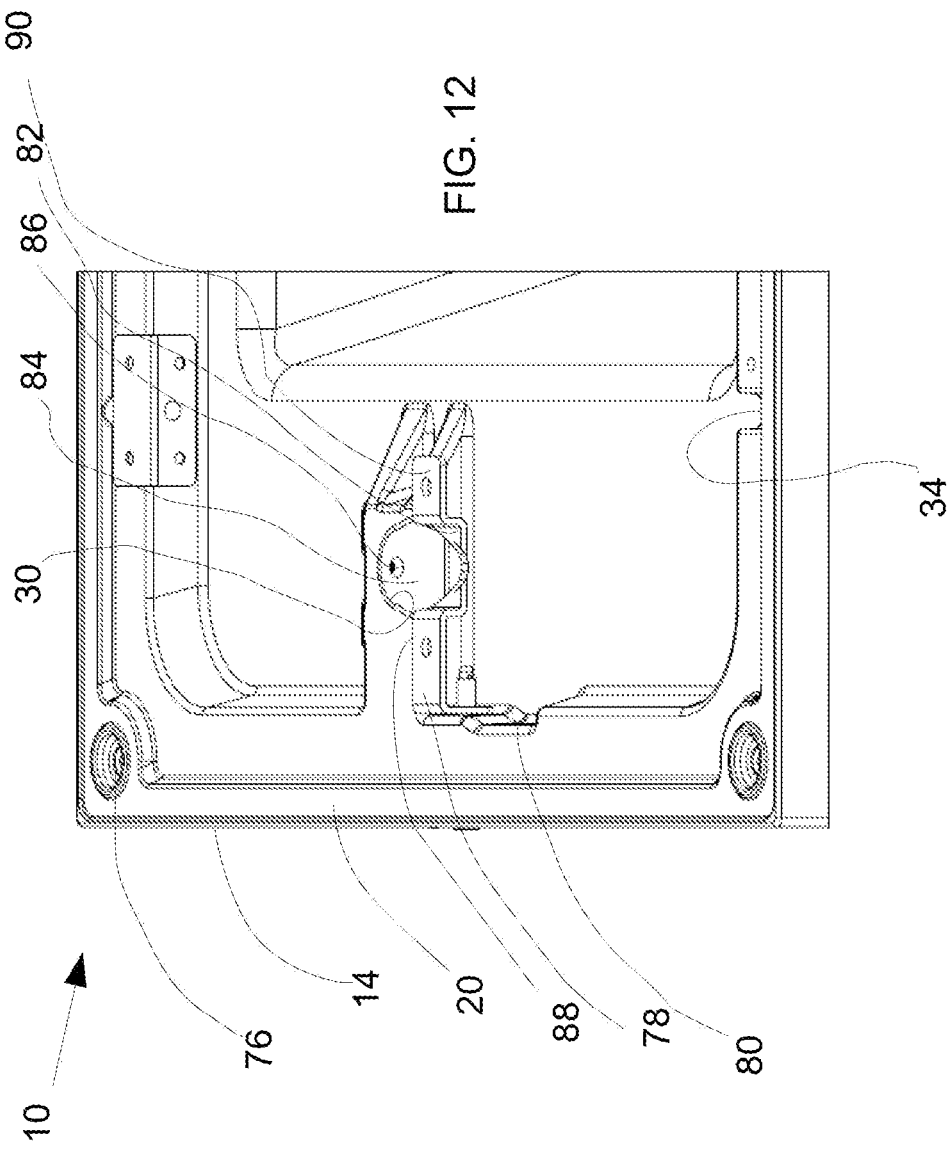

Referring to FIG. 12, the mounting saddle 30 is disposed on the bottom 20 and may be spaced from the end walls 18 and side walls 16. Tamper resistant glides 76 may be disposed in the corners of furniture piece 10. The furniture piece 10 may be attached to a floor or a wall in a similar fashion using a building bracket 78 and a tab 84. Building bracket 78 may comprise a pin flange 80 and a tab flange 82. Tab 84 may be attached to furniture 10 by screw 86 extending through tab 84 and into screw hole 74 (FIG. 11). Building bracket 78 may further comprise a first building flange 88 and a second building flange 90.

Figure 15:
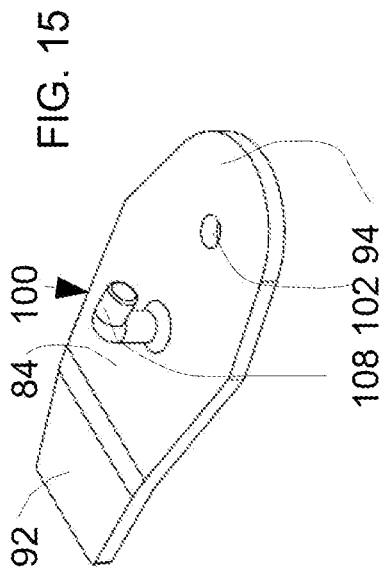
Figure 13:
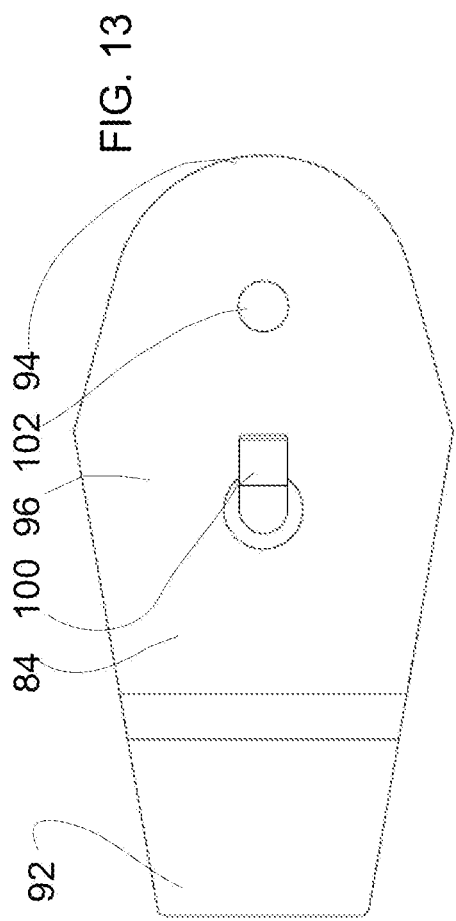
Figure 14:
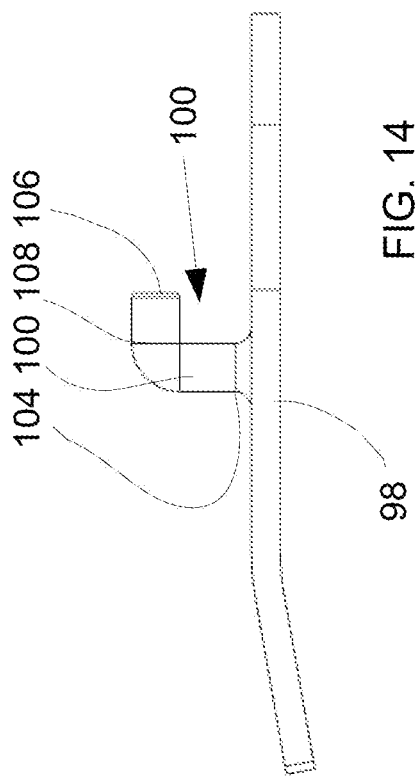

Referring to FIGS. 13-15, the shoe or tab 84 may further comprise a bracket end 92, a furniture end 94, a furniture side 96, a building surface side 98, a bolthole 102, and support finger 100. The support finger 100 is disposed on the furniture side 96 of tab 84. in a generally perpendicular orientation to furniture side 96. Support finger 100 may be disposed between bolt hole 102 and bracket end 92. Support finger 100 may comprise a first end 104 and a second end 106. First end 104 is attached to top or furniture side 96 in a generally perpendicular orientation. Second end 106 is spaced from tab 84 and may extend in a generally parallel orientation to the furniture side 96. Second end 106 is adapted to engage furniture 10. In the preferred embodiment, support finger 100 may further comprise a bend 108 between first end 104 and second end 106.

Referring to FIGS. 16-19, the building bracket 110 may comprise a first and second building flange 112, 114, a tab flange 116, and a pin flange 118. The first building flange 112 may be adapted to attach to a building surface such as floor or wall by bolt holes 124, 126 formed in the first and second building flanges 112, 114. The tab flange 116 may comprise a first and second spacer 115 and bar 117. The bar 117 spaced from the floor. A locking collar 120 may be attached to pin flange 118. Pin flange 118 may comprise a first end 127, a second end 128 and a pin hole 130. First pin flange end 127 on the first building flange 112. Second pin flange end 128 may be spaced from first building flange 112. Pin flange 118 may be disposed generally perpendicular to first building flange 112. Locking collar 120 may be disposed on pin flange 118 between first pin flange end 127 and second pin flange end 128. Locking collar 120 may comprise a hollow tube welded or other wise connected to pin flange 120. Locking collar 120 may be disposed in a generally concentric orientation with pin hole 130. Locking collar 120 may comprise a pin chamber 132, a flange end 134 and a pin end 136. Flange end 134 may be attached on the locking side 138. Pin end 136 may be spaced from the locking side 138. Pin chamber 132 is orientated generally concentric with the pin hole 130. Tab flange 116 may be disposed between first and second building surface flanges 112, 114.

Referring to FIGS. 20, 21, an elongate connector 149 may comprise a ball pin 150 comprising a shaft 152, an pin outside 154, a ball hole 156, a proximal end 158 and a distal end 160. Shaft 152 may comprise a hollow conduit 162 opening to the proximal end 158 and extending in the shaft 152 to the ball hole 156. Ball hole 156 extends from pin outside 154 to hollow conduit 162. Proximal end 154 may comprise a flange 164 comprising a mounting surface side 166 and a locking side 168. Retractable ball 170 may be disposed in hollow conduit 160 adjacent to ball hole 156. Ball retractor 174 may be slidingly disposed in hollow conduit 162. Ball retractor 174 may comprise retractor engagement 176 adjacent to proximal end. Ball retractor 174 bears against retractable ball 170. Spring 172 in hollow conduit 162 bears against shaft 152 and ball retractor 174. Spring 172 is adapted to urge ball retractor 174 to bear against retractable ball 170 to urge retractable ball 170 to nest in ball hole 156 wherein ball 170 extends through hole 156. Ball hole 156 may be formed adjacent the distal end 160. Retractable ball 170 is disposed in the hollow conduit 160 adjacent to ball hole 156 and may extend from the ball hole 156 in the locked position 178. In locked position 178 spring 172 bears against shaft 152 and ball retractor 174 thereby urging retractable ball 170 into the ball hole 156 extending from pin outside 154.

Continuing to refer to FIG. 21, a retractor tool 180 may comprise a shaft 182, an engagement end 184 and a tool shoulder 186. Engagement end 184 may comprise a threaded shaft adapted to thread into ball retractor 174. Engagement end engages ball retractor 174 by threadable engagement whereby tool shoulder 186 bears against mounting surface side 166 threadable engagement urging ball retractor 174 to traverse toward proximal end 158 urging retractable ball 170 to move out of ball hole 156 and into hollow conduit 162 to a non-locking position 188 wherein retractable ball 170 is not nested in ball hole 156.

Referring to FIGS. 22-24, a pin tube 200 adapted to receive elongate connector 149 (FIG. 21) may comprise comprises a hollow tube 204, a tube outside 206, a tube inside 208, a shell end 210, a retractor seat 211 and a pin flange end 212. Shell end 210 may comprise a shell flange 214 and retractor seat 211. Shell flange 214 may further comprise shell side 213.*

Referring to FIGS. 25-27 the building bracket 110 is engaged to tab 84 at bracket end 92. Pin tube 200 bears against pin flange 118 on building bracket 110. Distal end 160 extends through pin flange 118 having extended portion 170 of retractable ball 170 extending from pin hole and engaging pin flange 118 on locking side 230. Pin tube 200 extends from mounting surface side 232 of pin tube 200. Barb 201 may be formed on pin tube 200 to hold pin tube 200 in outer shell 36.

Figure 28:
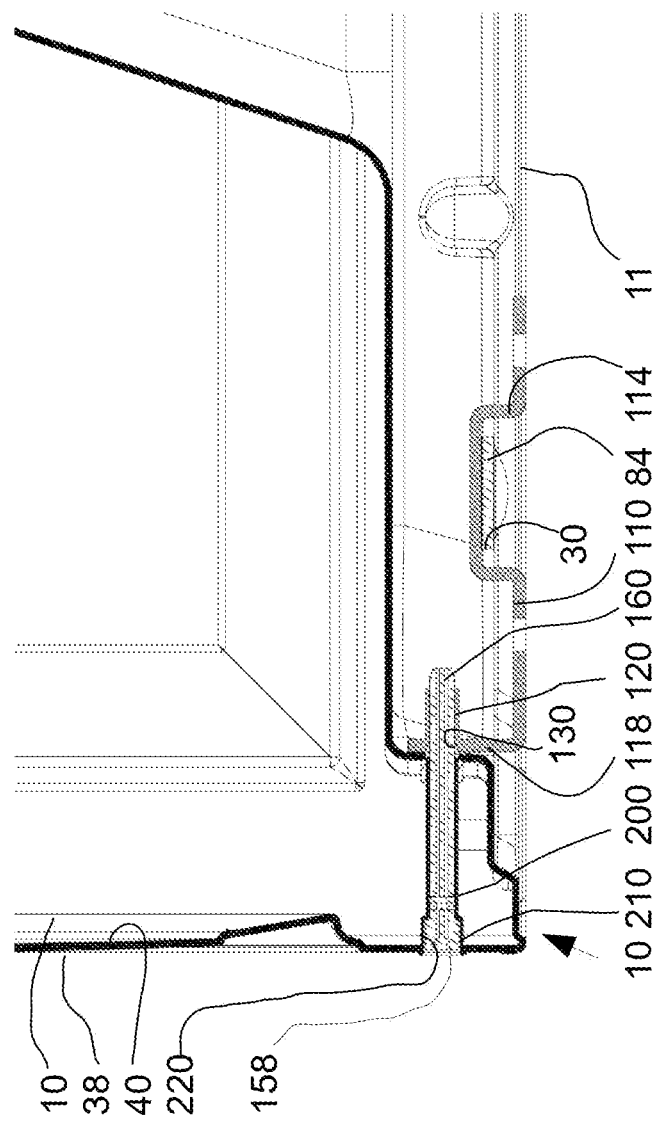
Figure 29:
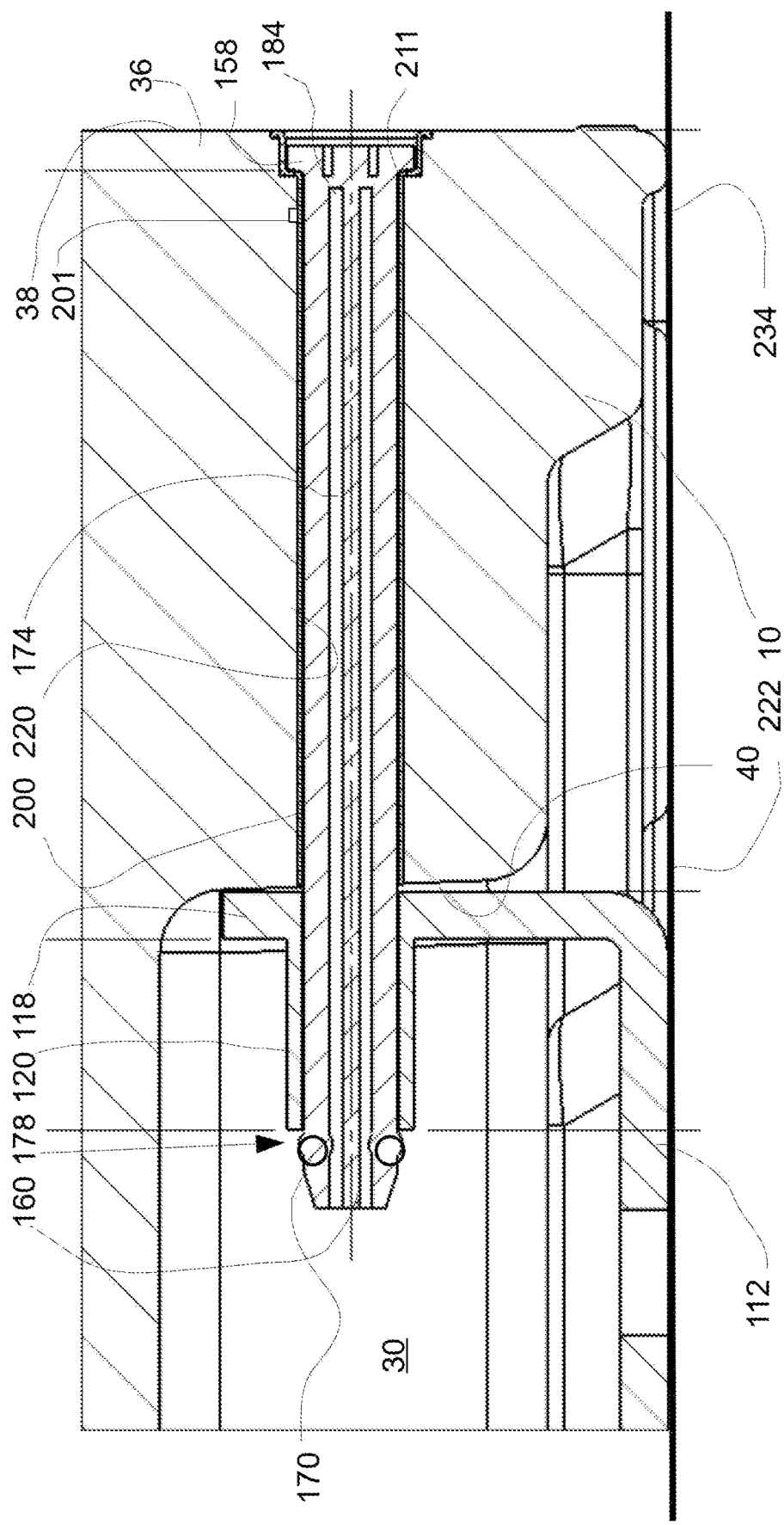
Figure 41:
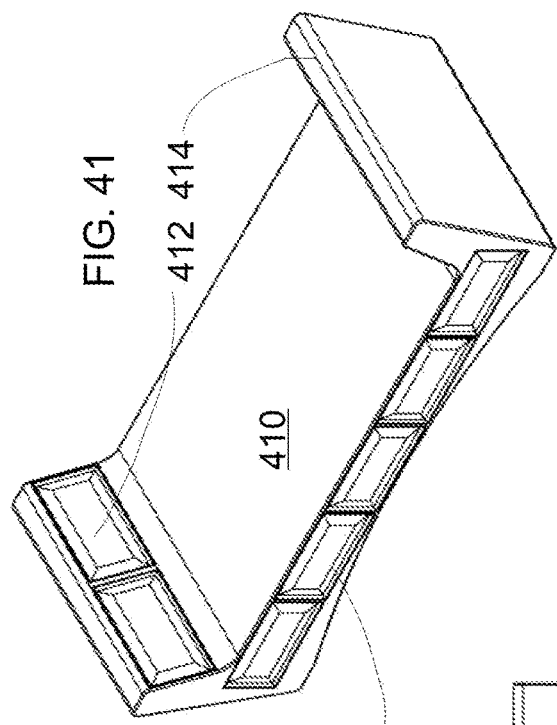
Figure 42:
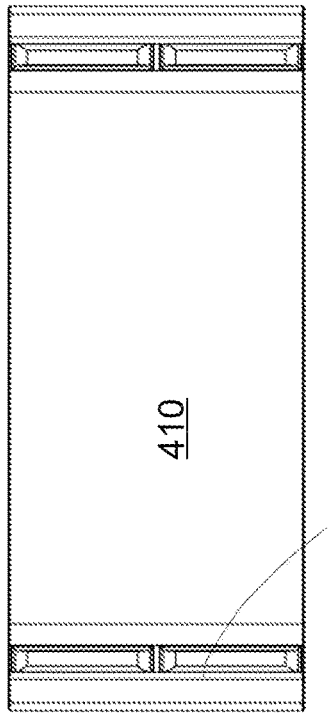
Figure 45:
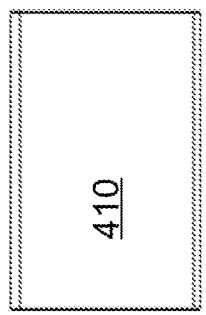
FIG. 45 is an end elevation view of the bed of FIG. 40.
Figure 43:
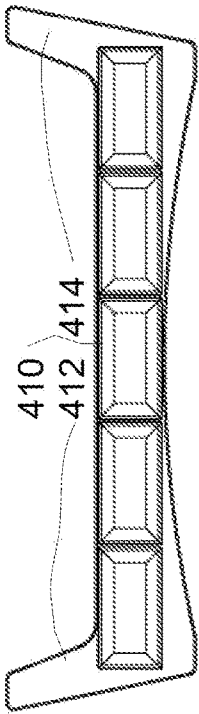
Figure 44:
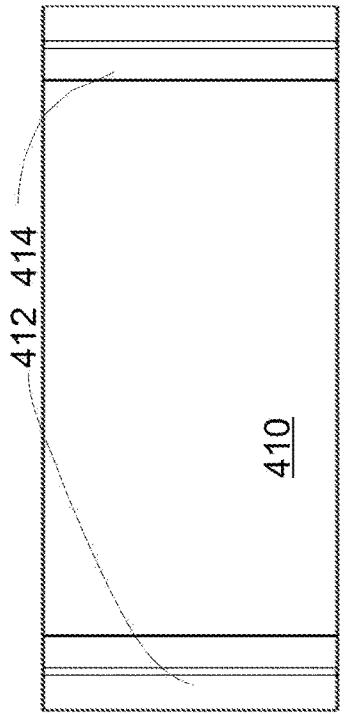
FIG. 44 is a bottom plan view of the bed of FIG. 40.
Figure 65:
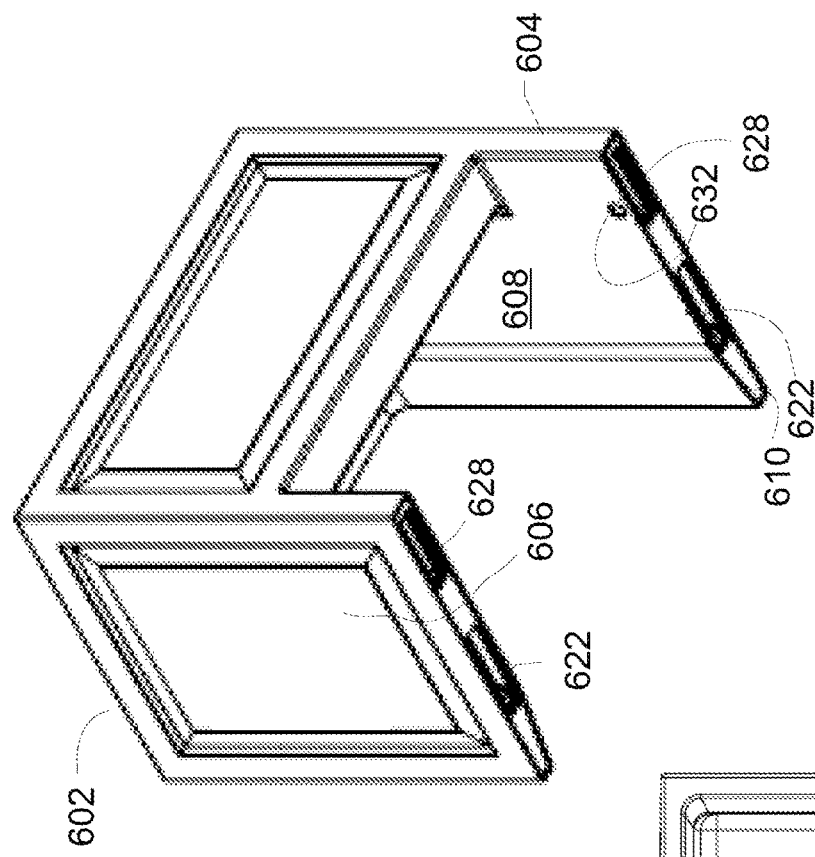
FIG. 65 is a front perspective view of the desk of FIG. 63 with wood-grain finish.
Figure 64:
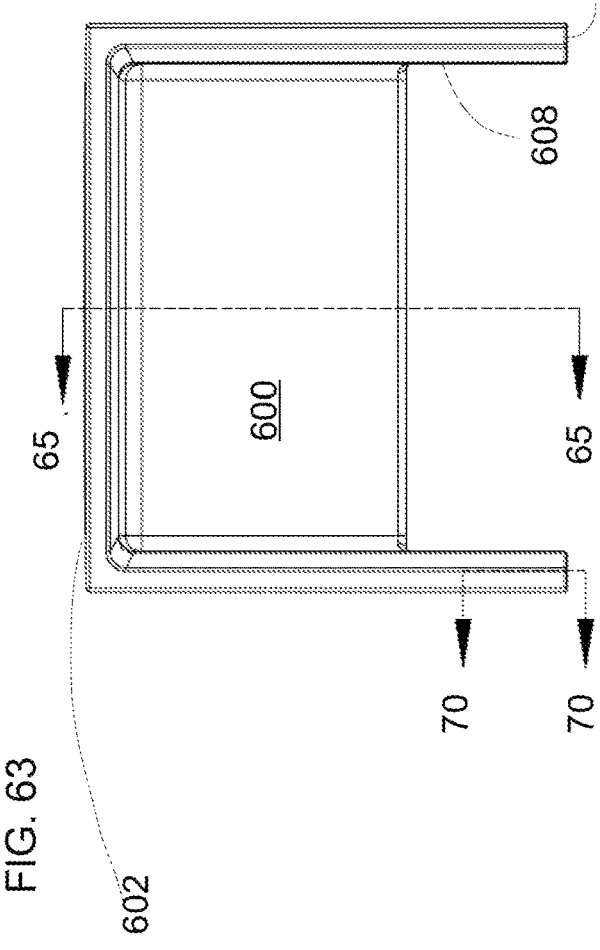
FIG. 64 is a front plan view of the desk of FIG. 63.
Figure 63:
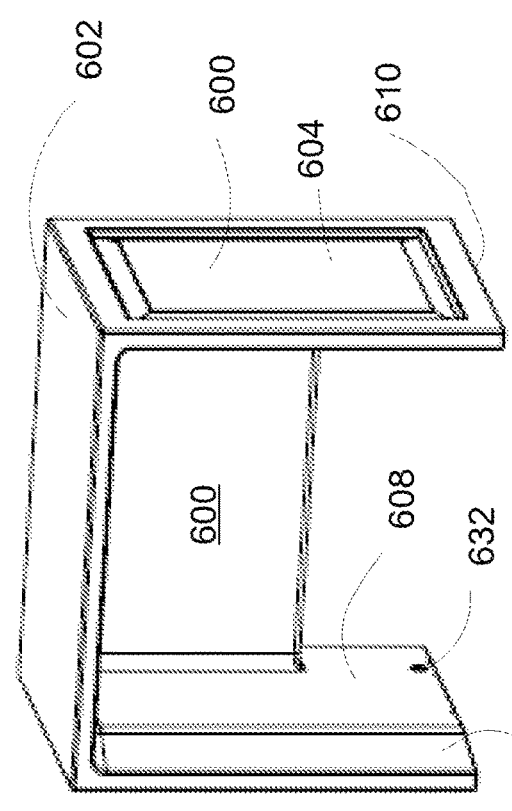
FIG. 63 is a top perspective view of an intensive use desk.

Referring to FIGS. 28 and 29, the furniture 10 has mounting hole 220 drilled from shell outside 38 to shell inside 40 proximate mounting saddle 30. Pin tube 200 is disposed in the mounting hole 220 having the proximal end engaged to the shell and the distal end extending through the pin tube 200 through the pin hole in the pin flange to the mounting side of the pin flange 118. the locking collar 120 is disposed on the mounting side of the pin flange. The extending portion 170 extends from ball hole and engages locking tube 120. Proximal end 158 of the elongate connector bearing on the connector flange 211. Ball retractor 174 bearing on retractable ball 170 and extending to proximal end of pin tube 200. Engagement end 184 is disposed adjacent to proximal end of pin tube 200. Barb 201 is adapted to engage outer shell 36.

Referring to FIGS. 30-35, dog leg tab 221 may comprise furniture end 222, and bracket hook 224. Dog leg tab 221 attaches to bottom 20 as tab 84 discussed with respect to FIG. 25. Tab seat 225 formed in mounting saddle 30 is adapted to receive furniture end 222 with screw 227 extending through dog leg tab 221 into furniture 10. Dog leg tab 221 may be oriented toward end wall 16 in coordination with first building bracket 110 and second building bracket 232, dog leg tab 221 may be used to attach furniture 10 shown as bed 12 to floor 234 between first wall 236 and second wall 238 forming corner 240 by the steps:

1. attach first and second building brackets to floor 234.
2. attach tab 84 to first mounting saddle 30 and dog leg tab 221 to second mounting saddle 237.
3. drill mounting hole 220 from shell outside 38 to mounting saddle 30.
4. push end of bed with dog leg hook to engage second building bracket 232 with bracket hook 230.
5. push bed to an orientation having end wall 16 parallel to first wall 236 disposing tab flange between bracket hook 230 and furniture end 222.
6. Insert pin tube 200 in mounting hole 220.
7. Insert ball pin in pin tube having shaft in pin hole on pin flange 118.
8. Engage ball retractor with retractor tool to urge retractable ball into hollow conduit.

9. Insert ball pin into locking collar 120 having ball hole adjacent locking end 136.

Referring to FIGS. 35-39 an alternative intensive use bed 310 may comprise foot risers 312, head risers 314, raised panel design 316 concealing storage 318. foot risers 312 and head risers 314 may further comprise linking surface 318 to allow a second bed 310 to be stacked in a bunk bed configuration.

Referring to FIGS. 41-45 an alternative intensive use bed 410 may comprise foot risers 412, head risers 414, raised panel design 416 concealing storage 418.

Referring to FIGS. 46-49 a night stand 450 may comprise a front 452, a back 454, a top 456, a pair of sidewalls 458 and a bottom 460. A mounting saddle 420 may be formed in bottom 460. A concealed floor attachment device may comprise a building bracket 110 having a pin flange 118 and a tab flange 116 attached to floor 234. Mounting hole 220 formed in shell extends into mounting saddle 420.

Referring to FIGS. 50-54, a book shelf 500 may comprise a top 502, a bottom 504, a pair of side walls 505 and a front 506. A mounting surface 508 chosen from the top 502, one side 505, bottom 504, or back 510 may further comprise a mounting saddle 520 formed on the shell outside 512. The mounting saddle 520 may comprise a tab seat 522 having a screw hole 523 extending into the shell 524. For floor 234 attachment, the mounting saddle 520 may be disposed on the bottom 504.

Referring to FIGS. 55-56, the book shelf 500 may comprise a mounting surface 508 chosen as the bottom 504 comprising a mounting saddle 520 comprising a tab seat 522. A concealed floor attachment device 525 may comprise a building bracket 110 having a pin flange 118 and a tab flange 116 attached to floor 234. Mounting hole 220 formed in shell extends into mounting saddle 420.

Referring to FIGS. 57-62, intensive use furniture 10 may be configured as a wardrobe 550. Wardrobe 550 may comprise a ligature resistant sloping top 552, a ligature resistant door 554 having a closed hinge connection 556 to wardrobe front 558 and a releasable hinge 560 configured to break away from wardrobe 550 if a weight of more than a predetermined weight is applied to the handle side 562 of door 554.

Referring to FIGS. 63-70, intensive use furniture 10 may be configured as a desk 600. The desk comprising a writing surface 602 a first leg 604, a second leg 606, and a mounting saddle 620. Each leg 604, 606 comprises an inside surface 608, a bottom 610 and an outside surface. The legs 604, 606 attached to the writing surface 602. A mounting saddle 620 formed in the bottom 610. The mounting saddle 620 comprising a flange opening 622 and a bolt tab pocket 628. The flange opening 622 comprising a flange shelf 624 disposed generally horizontal and adapted to engage a sliding flange 626. The bolt tab pocket 628 comprising an opening 630 into the bottom 610 and a bolt hole 632. The bolt hole 632 extending from the inside surface 608 to the bolt tab pocket 628.

Continuing to refer to FIGS. 69-70, mounting tab 640 is adapted to mount on flange shelf 624 in a generally horizontal orientation. Sliding flange 626 may comprise a z-shaped bracket having a first leg 632 on the floor 324, a second leg 634 angled upward from the floor supporting engagement leg 636 in a generally horizontal orientation. Engagement leg 636 is adapted to extend into flange opening 622 to engage mounting tab 640 wherein mounting tab is between engagement leg 636 and floor 324. Desk bracket 650 may comprise a floor flange 652 and a bolt flange 654. Floor flange 652 is adapted to attach to floor 324 by bolts extending through floor flange 652. Bolt flange 654 comprises a first end 656 on floor flange 652 and s second end 658. Flange hole 660 extends through bolt flange 654 in concentric position with bolt hole 630 when desk 600 is disposed having bolt flange 654 extending into bolt tab pocket 628. Threaded nut 662 is attached to bolt flange opposite bolt hole 630 concentric with flange hole 660. Bolt 661, having tamper resistant head 664 is inserted into bolt hole 630 through flange hole 660 and threadably engages threaded nut 662 to attach desk 600 to floor 324.

Continuing to refer to FIGS. 69-70-mounting tab 640 is attached to shelf 624. Sliding flange 626 is attached to floor 324. Desk bracket 650 is attached to floor 324 by floor flange 652. Desk leg 604 is placed over sliding flange and desk bracket 650 wherein sliding flange 626 is in flange opening 622 and desk bracket 650 is in bolt tab pocket 628. Desk leg 604 is moved in a direction toward desk back 654 urging sliding flange 626 to engage mounting tab 640 wherein leg 636 is disposed between mounting tab 640 and writing surface 602. Bolt hole 630 aligns with flange hole 660. Bolt 661 is inserted through bolt hole 630 to threadably engage nut 662 to secure desk to floor 324.

Although the description above contains many specifications, these should not be construed as limiting the scope of the invention but as merely providing illustrations of some of the embodiments of this invention. Thus, the scope of the invention should be determined by the appended claims and their legal equivalents rather than by the examples given. Further, the present invention has been shown and described with reference to the foregoing exemplary embodiments. It is to be understood, however, that other forms, details, and embodiments may be made without departing from the spirit and scope of the invention which is defined in the following claims.

The invention claimed is:

1. A concealed attachment device for use attaching furniture to a building surface, the furniture comprising an outer shell, a mounting surface and a shell mounting hole, the outer shell comprising a shell outside, a shell inside and a hollow shell interior, the shell mounting hole extending from the shell outside to the mounting surface, the shell mounting hole is generally parallel to the building surface, the concealed attachment device comprising:

a building bracket, the building bracket comprising a first building flange and a pin flange, the pin flange comprising a first end, a second end and a connector hole, the first pin flange end on the first building flange, the pin flange disposed generally perpendicular to the first building flange, the first building flange on the building surface, the pin flange bearing against the mounting surface;

an elongate connector, the elongate connector having a shaft, a proximal end and a distal end, the proximal end on the outer shell, the shaft in the shell mounting hole, the distal end removably connected to the pin flange;

a furniture screw; and a shoe, the shoe comprising a bracket end, a furniture end, a furniture side, a building surface side, a shoe bolt hole and a support finger, the furniture end on the mounting surface, the shoe bolt hole extending through the furniture end from the furniture side to the building surface side, the furniture screw in the shoe bolt hole, the furniture screw in the mounting surface, the support finger on the furniture side, the support finger disposed in a finger hole on the mounting surface, the bracket end on the building bracket.

2. The concealed attachment device of claim 1, further comprising a shoe flange on the building bracket, the shoe flange bearing on the shoe, the shoe flange between the bracket end and the mounting surface.

3. The concealed attachment device of claim 2, wherein the building bracket further comprises a second building flange, the shoe flange between the first building flange and the second building flange.

4. The concealed attachment device of claim 3, wherein the elongate connector comprises a ball pin and a retractor tool, the retractor tool engaged to the ball pin to release a retractable ball of the ball pin.

5. The concealed attachment device of claim 4, wherein the shoe further comprises a first edge and a second edge, the first edge extending from the furniture end to the bracket end, the second edge extending from the furniture end to the bracket end, the first edge spaced from the second edge, the shoe flange further comprising a first spacer, a second spacer and a shoe bar, the first spacer on the first building flange, the second spacer on the second building flange, the shoe bar on the first spacer, the shoe bar on the second spacer, the shoe bar on the bracket end, the first edge on the first spacer, the second edge on the second spacer whereby the shoe attaches the furniture to the building bracket.

6. The concealed attachment device of claim 1, further comprising a pin tube, the pin tube in the mounting hole, the pin tube on the pin flange, the elongate connector in the pin tube.

7. The concealed attachment device of claim 6, wherein the pin tube further comprises a tube outside, a shell end and a pin flange end, the tube outside extending from the shell end to the pin flange end, the shell end comprising a tube flange and a barb, the tube flange on the shell end, the barb on the pin tube between the tube flange and the pin flange end, the barb extending from the tube outside, the barb on the outer shell whereby the shell outside is between the barb and the tube flange attaching the pin tube to the outer shell.

8. The concealed attachment device of claim 7 wherein the pin flange end is adjacent to the pin flange.

9. The concealed attachment device of claim 8, wherein the mounting hole further comprises a countersunk tube flange surface, the tube flange surface between the shell inside and the shell outside, the tube flange on the tube flange surface.

10. The concealed attachment device of claim 1, wherein the elongate connector comprises a ball pin, the ball pin comprising a retractable ball, the shaft comprising a hollow conduit and a pin outside, a ball hole in the hollow conduit, the ball hole extending to the pin outside, the ball hole adjacent the distal end, the retractable ball in the shaft, the retractable ball adjacent to the ball hole, the pin flange further comprising a mounting surface side and a locking side, the ball hole between the distal end and the locking side.

11. The concealed attachment device of claim 10, further comprising a ball retractor in the proximal end, the ball retractor on the retractable ball, the ball retractor adapted to urge the retractable ball between a recessed position in the hollow conduit and a locking position in the ball hole wherein the ball extends from the pin outside.

12. The concealed attachment device of claim 10, further comprising a locking collar on the pin flange, the locking collar comprising a pin chamber, a flange end and a pin end, the flange end on the locking side, the pin end spaced from the locking side, the pin chamber generally concentric with the mounting hole, the shaft in the pin chamber, the distal end spaced from the pin end, the ball hole between the distal end and the pin end.

13. The concealed attachment device of claim 12, wherein the retractable ball disposed in the ball hole, the ball bearing against the pin end.

* * * * *